(12) United States Patent
Tajima

(10) Patent No.: US 6,805,840 B1
(45) Date of Patent: Oct. 19, 2004

(54) APPARATUS FOR INTEGRATED PROCESS OF MAGNETIC PARTICLES AND METHOD OF CONTROLLING THE SAME

(75) Inventor: Hideji Tajima, Yanokuchi-Inagi (JP)

(73) Assignee: Precision Systems Science Co., Ltd., Tokyo (JP)

( * ) Notice: Subject to any disclaimer, the term of this patent is extended or adjusted under 35 U.S.C. 154(b) by 0 days.

(21) Appl. No.: 09/646,653

(22) PCT Filed: Mar. 18, 1999

(86) PCT No.: PCT/JP99/01365

§ 371 (c)(1),
(2), (4) Date: Sep. 18, 2000

(87) PCT Pub. No.: WO99/47267

PCT Pub. Date: Sep. 23, 1999

(30) Foreign Application Priority Data

Mar. 19, 1998 (JP) .......................................... 10-070980

(51) Int. Cl.[7] ................................................. B01L 3/02
(52) U.S. Cl. .......................... 422/100; 422/99; 422/101; 422/186.01; 436/174; 436/177; 436/180; 436/525; 436/526; 210/695
(58) Field of Search .......................... 422/99, 100, 101, 422/102, 186.01; 436/174, 177, 180, 525, 526; 210/222, 223, 695

(56) References Cited

U.S. PATENT DOCUMENTS

| | | | | |
|---|---|---|---|---|
| 4,292,920 A | * | 10/1981 | Smith et al. ................. | 118/425 |
| 4,751,053 A | * | 6/1988 | Dodin et al. ................. | 422/101 |
| 5,647,994 A | * | 7/1997 | Tuunanen et al. .......... | 210/695 |
| 5,702,950 A | * | 12/1997 | Tajima ......................... | 436/49 |
| 5,705,062 A | * | 1/1998 | Knobel ......................... | 210/205 |
| 5,942,124 A | * | 8/1999 | Tuunanen .................... | 210/695 |
| 5,976,369 A | * | 11/1999 | Howe et al. ................. | 210/222 |
| 6,133,037 A | * | 10/2000 | Tajima ......................... | 436/49 |
| 6,187,270 B1 | * | 2/2001 | Schmitt et al. ............. | 422/101 |
| 6,207,463 B1 | * | 3/2001 | Tuunanen .................... | 436/526 |
| 6,231,814 B1 | * | 5/2001 | Tajima ......................... | 422/101 |
| 6,455,325 B1 | * | 9/2002 | Tajima ......................... | 436/526 |
| 6,509,193 B1 | * | 1/2003 | Tajima ......................... | 436/49 |

* cited by examiner

*Primary Examiner*—Jill Warden
*Assistant Examiner*—Dwayne K Handy
(74) *Attorney, Agent, or Firm*—Haynes and Boone, LLP

(57) ABSTRACT

The present invention relates to an apparatus for an integrated process of magnetic particles and a method of controlling the same, for executing a process for magnetic particles incorporated in a fluid in an integrated state. The present invention aims to provide an apparatus for an integrated process of magnetic particles and a method of controlling the same, that can promptly and efficiently process all together in high precision, with the process of magnetic particles integrated.

The apparatus for an integrated process of magnetic particles comprises a reservoir body provided with plural pit-like reservoirs for storing a drawn liquid arranged in a matrix, a sliding body with jutting plural sliding projections sliding through the reservoirs and capable of moving vertically to and from the reservoir body, plural nozzles attached to the lower parts of the reservoirs and capable of passing the liquid therethrough, a magnetic force device capable of magnetization and demagnetization having plural through sections in which is inserted each nozzle and having a wall part in contact with or near the outer side surface of the nozzle, with the nozzles inserted thereinto, wherein each wall part has two divided wall parts being apart from one another in such a manner that the divided wall parts have opposite polarities by magnetization, respectively.

37 Claims, 22 Drawing Sheets

F I G. 1 1
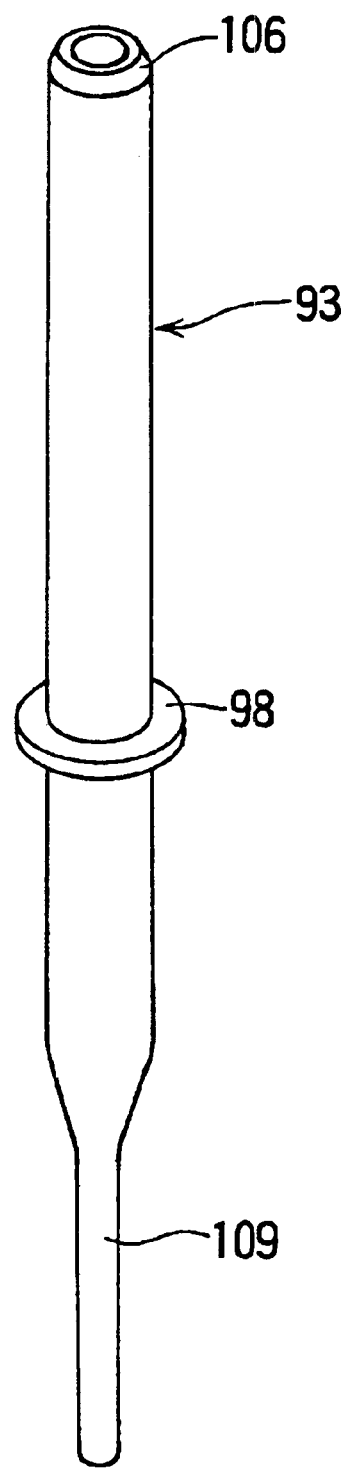

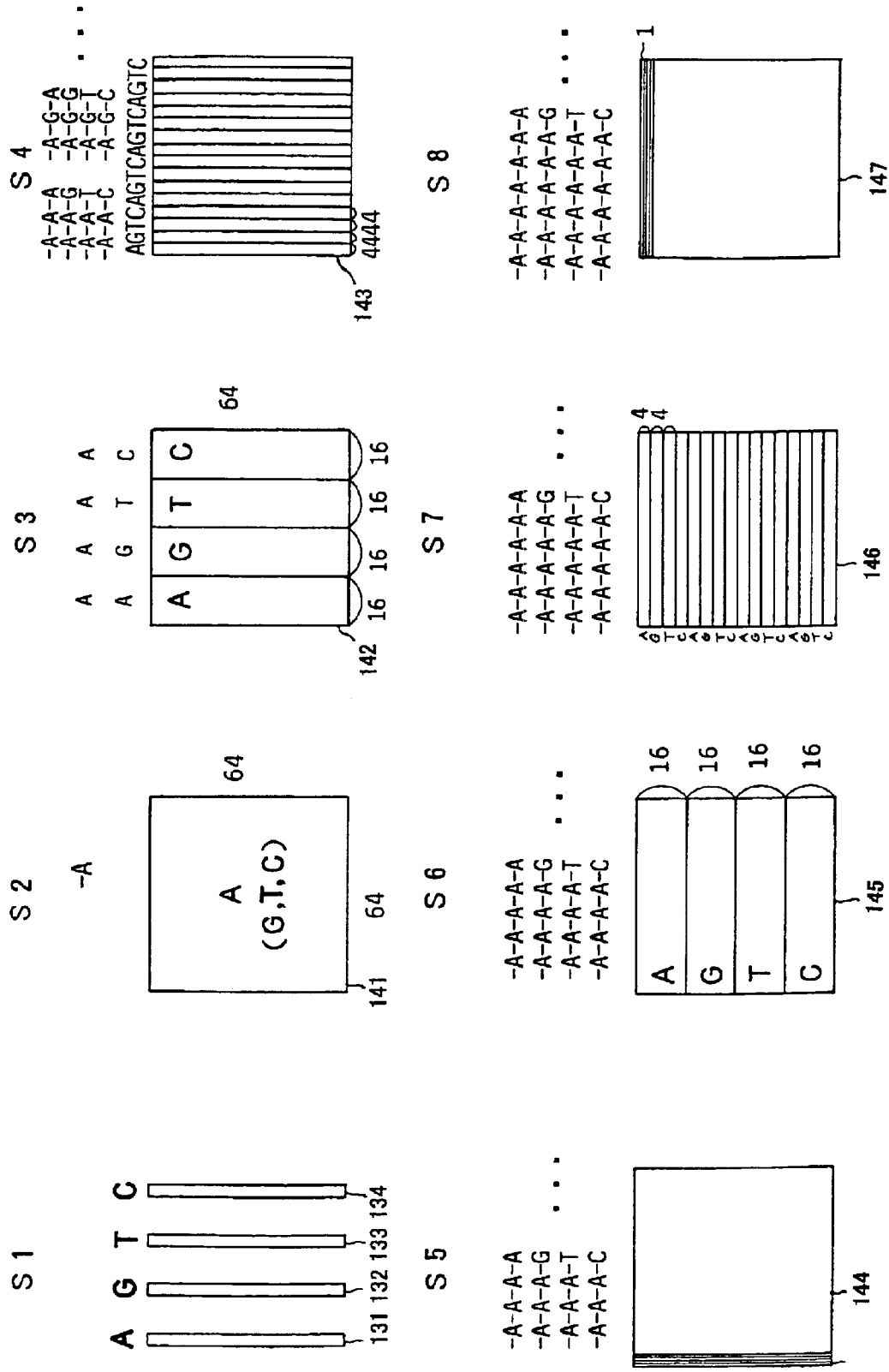

FIG. 13
(a)
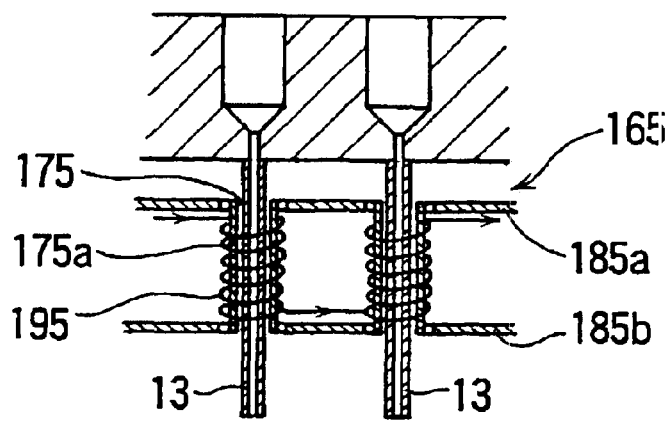
(b)
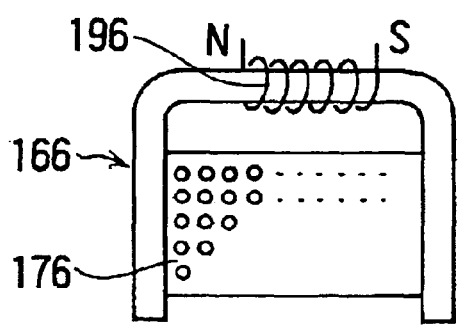
(c)
(d)
(e)
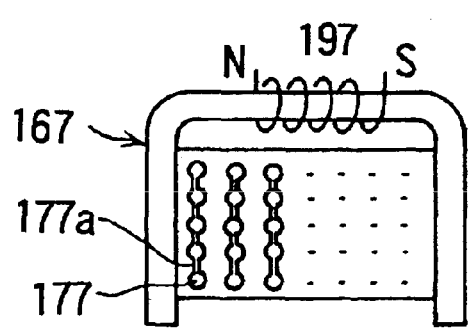
(f)
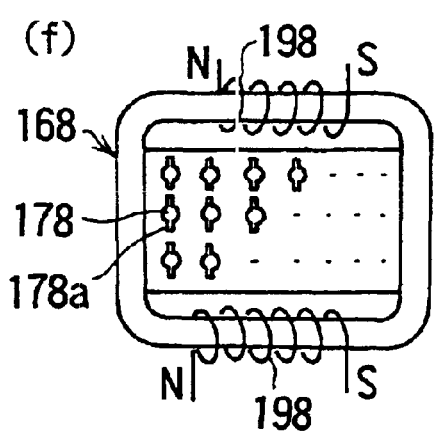
(g)
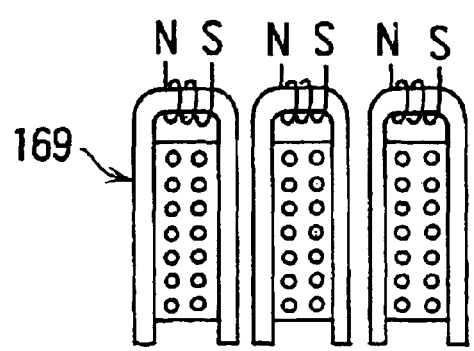

FIG. 16
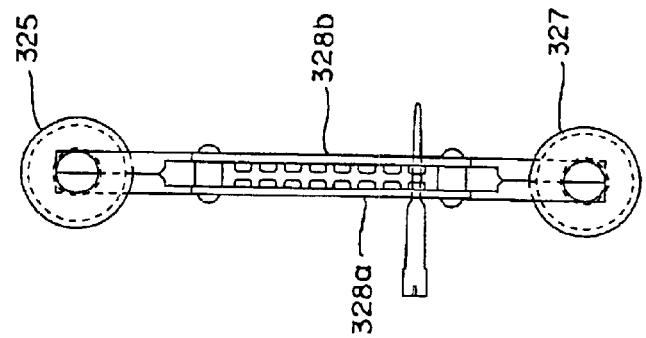
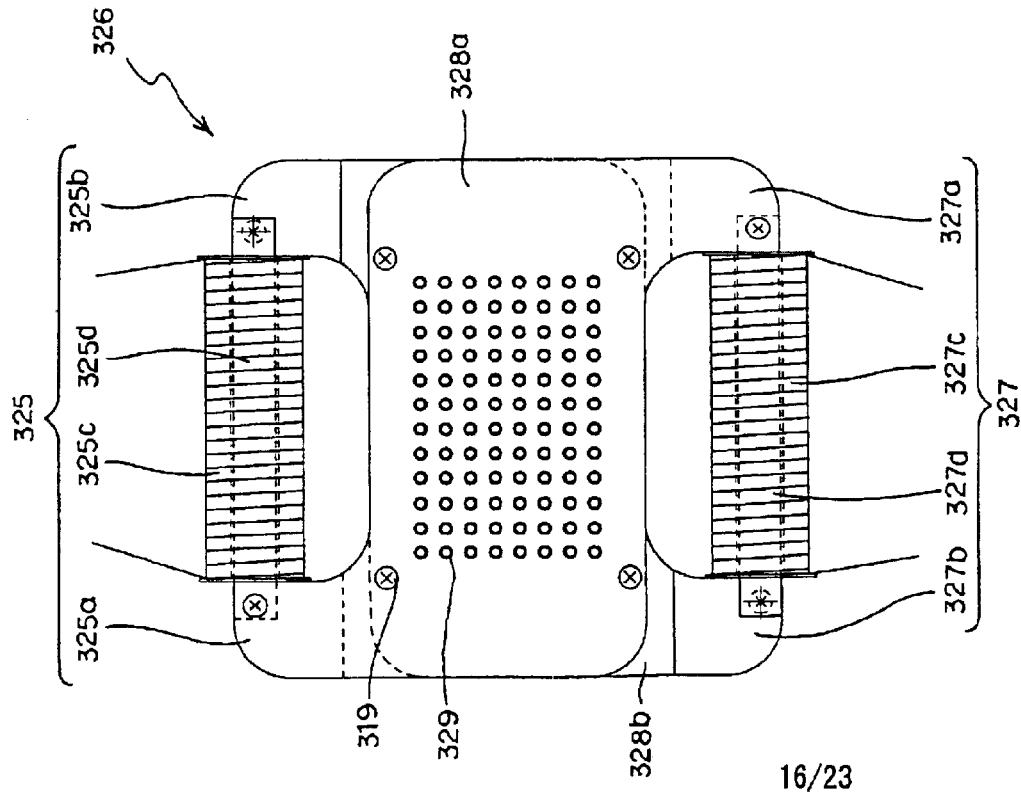

APPARATUS FOR INTEGRATED PROCESS OF MAGNETIC PARTICLES AND METHOD OF CONTROLLING THE SAME

FIELD OF THE INVENTION

The present invention relates to an apparatus for an integrated process of magnetic particles and a method of controlling the same. Particularly, the present invention relates to an apparatus for an integrated process of magnetic particles and a method of controlling the same, which can execute processes such as reaction, separation, fixing quantity, dispensation, clarification, concentration, agitation, suspension, dilution, and operations such as observation, extraction, recovery, isolation, and indications in regard to for example, immune substances such as antibodies or antigens, genetic substances (DNA, RNA, m-RNA and so on), bacillus, and other useful substances such as medicines, or target substances, for medical treatment, inspection, diagnosis, medical care, research, quantitative analysis, qualitative analysis and so on in all manner of fields such as medical science, agricultural science, engineering, scientific fields, pharmaceuticals, by using a fluid incorporating magnetic particles and capable of being processed in large numbers in a vessel such as a microplate.

BACKGROUND OF THE INVENTION

Currently, there is a pipette device shown in FIG. 21. As shown in this view, the pipette device has a magnet driving device for controlling to drive a magnetic source M and a holding body V The magnetic source M having a magnet section and the holding body V having a holding section, are rotatably mounted in an up-down mechanism of the pipette device in such a manner that they can approach and go away from one another.

When the up-down mechanism O moves vertically, as shown in FIG. 21, the magnetic source M and the holding body V move in obedience to movement of rollers $R_A$ $R_B$ of the up-down mechanism O so that they close in a way that they hold a tip between them. As a result, the magnetic source M and the holding body V can simultaneously come in contact with the pipette tip T in a manner that they hold the pipette tip T, and the magnetic source M can surely approach to the tip T and separate from the tip T.

In order to execute a process for large numbers of substances such as combinatorial chemistry, DNA function analysis, or automatic measurement of immune substances, many pipette tips are necessary. Currently, a multiplex pipette device having many pipette tips arranged in a line is used, as shown in FIG. 22. In regard to the conventional pipette device capable of processing magnetic particles, not only pipette tips but also mechanisms ($M_1$, $M_2$, $M_3$, $M_4$, $V_1$, $V_2$, $V_3$, $V_4$) which are mounted per each pipette tip for applying and removing a magnetic field to and from the pipette tip respectively by driving a magnet, need to be multiply provided and linked.

Therefore, though such a multi-linking using tips arranged in a line is embodied, such an integration as applying al magnetic filed to many lines of nozzles simultaneously by using the device causes the problem that the apparatus is scaled up in size and processes cannot be executed in an integrated state.

Particularly, when a large number of samples are handled and the wells (plate holes of a microplate) of a vessel are for example, 96 wells or 384 wells or more, driving sections for applying and removing the magnetic field to and from the nozzles and magnetic particles, need be integrated in high density. However, since the driving section prevents integration, there is a problem that the process for magnetic substances cannot be integrated.

The present invention aims to resolve the aforementioned problems. A first object of the invention is to provide an apparatus for an integrated process of magnetic particles and a method of controlling the same, that can promptly and efficiently process all together in high, precision, with integration of the process of magnetic particles, by integrating nozzles and sections for driving sections for applying the magnetic fields to the nozzles.

A second object of the invention is to provide an apparatus for an integrated process of magnetic particles and a method of controlling the same, which integrates the process for the magnetic particles without using a magnet driving device having elements whose scale or action range is large, and which can execute the process of a large number of substances with a small scale and compact device.

A third object of the invention is to provide an apparatus for an integrated process of magnetic particles and a method of controlling the same, in which a plurality of elements are integrated, the structure of elements per unit of integration is simplified and the cost performance is high.

A fourth object of the invention is to provide an apparatus for an integrated process of magnetic particles and a method of controlling the same, which is suitable for a microplate having a plurality of wells, and which has such diversity and flexibility that it can be applied to various fields requiring processes for large numbers of substances such as combinatory chemistry, DNA function analysis, and automatic measurement of immune substances, and has diversity and flexibility.

A fifth object of the invention is to provide an apparatus for an integrated process of magnetic particles and a method of controlling the same, which can exclude human operations to the utmost and facilitates automatization, in a process for fluids.

A sixth object of the invention is to provide an apparatus for an integrated process of magnetic particles and a method of controlling the same, which can exclude mechanical movement to the utmost, can work at a low running cost, has a long life span, and is easily handled.

A seventh object of the invention is to provide an apparatus for an integrated process of magnetic particles and a method of controlling the same, which can complete whole steps within a confined space and can exclude influence between the space and the outer environment to the utmost, and which can reliably execute the process.

SUMMARY OF THE INVENTION

In order to resolve the above technical problems, a first aspect of the invention is an apparatus which comprises a drawing/discharging device for drawing and discharging a fluid, plural nozzles for passing the fluid therethrough while drawing and discharging, and a magnetic force device for applying and removing a magnetic field to and from the nozzles respectively with remaining stationary near each nozzle exterior.

The "drawing/discharging device" comprises for example, a plurality of separate cylindrical containers being bundled, or a block in which plural cylindrical containers are formed. Each container comprises for example, a drawing/discharging line, a plunger, an elastic body, bellows or a diaphragm, for drawing and discharging a fluid. "Fluid"

includes a liquid and a gas. It also includes a fluid incorporating or suspending solid substances such as magnetic particles or magnetic substances.

"Plural nozzles" are preferably arranged in a plane-like state for convenience sake, in which for example, a matrix-like state, a circular state and a two-dimensional state are included, but the plane-like state is not restricted to these examples.

"Nozzle" may be fixed to the drawing/discharging device, or may comprise a pipette tip that is detachably mounted to the drawing/discharging device directly or to a section fixed to the drawing/discharging device.

The pipette tip includes a disposable type and a cleaning and a recycling type. "Magnetic force device" serves to make the magnetic substances or magnetic particles suspended or incorporated in a liquid adhere to inner walls of the nozzles. Thus, a process for magnetic particles such as transferring, agitation, cleaning, separation, resuspension and so on can be executed. "Magnetic force device" is one that can simultaneously apply and remove a magnetic field to and from the nozzles respectively, in a manner that the neighborhood of the outer side of the nozzles remains stationary. The structure does not require a complicated mechanism near the outer side of the nozzles or a space for movement. Therefore, a plurality of nozzles can be densely integrated, instead. Hence, the process for the magnetic particles can be integrated, the apparatus can be scaled down, the space can be reduced, and the process can be efficiently executed. Furthermore, since large numbers of small quantity objects can have conditions being equal and uniform in time and space, the process for each small quantity object can be executed in high precision. Since a large number of small quantity objects can be simultaneously processed, the process can be sped up and efficiency of the process can increase.

Here, since neighborhood of "each nozzle exterior" remains stationary, the case where a moving mechanism for applying and removing the magnetic field, is mounted at a part outside of the neighborhood of the nozzle exterior is not excluded. Furthermore, the case where the magnetic force device moves not for the purpose of applying and removing the magnetic field, but for transportation of the entire apparatus, is not excluded.

The magnetic force device is constructed, for instance, so that a part of each nozzle or nozzle outer member is made of a magnetic material such as a para-magnetic material or a super para-magnetic material etc. which is magnetically connected to an electromagnet having a switch, or a magnetic source such as permanent magnet or electromagnet capable of detaching therefrom.

"Magnetic particles or magnetic substances" are processed so as to be able to combine with related substances such as target substances. The magnetic particles have a size of for example, about 0.1–100 μm, and combine with the related substances by holding the related substances in a porous material having a plurality of recesses in the magnetic particles, by adsorbing the related substances, or by reacting the related substances with substances coated or held in the magnetic particles. For example, the magnetic particles are made of a super para-magnetic substance. Furthermore, the magnetic force device may be fixed to the drawing/discharging device, or may be detachably mounted.

A second aspect of the invention is an apparatus for an integrated process of magnetic particles according to the first aspect of the invention, wherein the magnetic force device can apply and remove the magnetic force to and from the nozzles respectively by enabling magnetization and demagnetization in a nozzle outer member brought in contact with or being near the outer surface of the nozzle or at least a part of the nozzle, with remaining stationary near each nozzle exterior.

"Magnetization and demagnetization" implies that the magnetic material is magnetized under influence of the magnetic field and demagnetized without influence of the magnetic field.

With the present invention, since the magnetic force device can be simplified in structure, the structure of the entire apparatus can be simplified and the cost of the products can be reduced. Particularly, in the case of "enabling magnetization and demagnetization in at least part of the nozzle", since the necessary volume or the bottom area for magnetization and demagnetization is small, integration is improved much more.

A third aspect of the invention is an apparatus for an integrated process of magnetic particles according to the second aspect of the invention, wherein the magnetic force device comprises a magnetic member made of a magnetic material and provided with a plurality of through sections capable of taking insertion of nozzles, wherein the nozzle outer member is a wall of the through sections. With the present invention, a plurality of nozzles can be easily and densely integrated by a simple structure. Consequently, the cost of products can be reduced, and the apparatus can be made to be compact.

"Magnetic member" is made of for example, para-magnetic materials or super para-magnetic materials.

A fourth aspect of the invention is an apparatus for an integrated process of magnetic particles according to the second or the third aspect of the invention, wherein the nozzle outer member or a part of the nozzle comprises divided parts that are divided in two, wherein the divided parts are apart from one another in a manner that the divided parts have mutually opposite magnetic polarities.

The distance between the divided parts is one which can give an appropriate magnetic force within the nozzle. The distance is determined by considering the strength of the magnetic field of the magnetic source, the kinds of magnetic materials, the size of the through section, each location of the through section, or the distance from the magnetic source, the size of the magnetic force device, and the magnetic force necessary for the processes etc. When the distance between the divided parts is the shortest in the magnetic force device, the maximum magnetic force can be generated there compared to the sections having a longer distance between the divided parts.

With the present invention, the divided parts are apart from each other so that the lines of magnetic force can leak out in the places where required, and an appropriate magnetic force can be efficiently applied to the nozzle, without wastage, by leakage of the lines of magnetic force.

A fifth aspect of the invention is an apparatus according to the fourth aspect of the invention, wherein the magnetic force device comprises a magnetic source having an electromagnet or a permanent magnet, two magnetic plates made of magnetic material and connecting with the electromagnet or capable of connecting with the permanent magnet and capable of being magnetized and demagnetized, and mounted in face-to-face relationship in a low and a high position, plural through sections penetrating the two magnetic plates and capable of taking insertion of the nozzles, a pair of projections mounted in each through section, projecting to the opposite surface of each magnetic plate and made of magnetic materials, wherein the pair of the projections correspond to the nozzle outer member, and each projection corresponds to the divided parts and are apart from one another in such a manner that they have mutually opposite polarities by magnetization.

When an electromagnet is used as the magnetic source, generation and extinguishment of magnetic fields are executed by conducting and cutting off the electric currents, respectively. When a permanent magnet is used as the magnetic source, the magnetization and demagnetization can be executed by mounting and dismounting or touching and detaching. Touching and detaching are executed by for example, rotating a permanent magnet about an axis of rotation and touching or approaching, or separating the pole thereof to or from the magnetic member respectively.

"The magnetization and demagnetization" can be executed at positions far from each nozzle, without providing a driving mechanism or a drive space for each nozzle, by mounting and dismounting the permanent magnet to and from magnetic plates magnetically connecting with the wall parts mounted near each nozzle and made of magnetic material, or by conducting and cutting off the electric current. It thus follows that a plurality of nozzles can be arranged in an integrated state.

With the present invention, since the magnetic field being generated between the projections can be stronger than that, generated between the magnetic plates, the strong magnetic field leaking out between the projections can be applied to the nozzles, by mounting the projections projecting toward the opposite surfaces of the magnetic plates at a predetermined interval. "A predetermined interval" is the distance that does not affect magnetic fields irrelevant to the process and that allows the nozzle to penetrate the through section.

A sixth aspect of the invention is an apparatus according to the fifth aspect, wherein the through section comprises through holes penetrating through the magnetic plates and projecting vertically and capable of taking insertion therethrough by the nozzles, and each wall part of the mutually separated through holes has opposite polarity respectively.

With the present invention, the magnetic field can be efficiently applied to within the nozzle without waste.

A seventh aspect of the invention is an apparatus according to the fifth aspect, wherein the magnetic force device comprises one or more magnetic sources, the magnetic source comprises a coil and a magnetic element provided with the coil, and one end of the magnetic element is connected with one of the two magnetic plates and the other end thereof is connected with the other thereof.

With the invention, since each magnetic plate connects with only one end or the other end of the magnetic element serving as the magnetic source, the magnetic plates are not directly touched. Therefore, a stronger magnetic field can be generated between the divided parts whose distance is shorter than that between the magnetic plates.

An eighth aspect of the invention is an apparatus according to the seventh aspect, wherein the magnetic elements are mounted outside of the space which is formed by the magnetic plates.

With the invention, since the magnetic elements are mounted outside of the space sandwiched between the magnetic plates, the turn number of the coil is not restricted by the interval between the magnetic plates, and a strong magnetic force can be generated.

A ninth aspect of the invention is an apparatus according to the eight aspect, wherein the magnetic elements comprise a first part and a second part which are separately mounted, wherein one end of the first part connects with one of the two magnetic plates, the other end of the second part connects with the other magnetic plate, wherein the first part and the second part are overlapped and are wound by wire of a coil, or the other end of the first part and one part of the second part are connected with each end of the third part and wound by wire of the coil and made of magnetic material.

With the invention, the magnetic element and magnetic plate can be easily produced by separating the magnetic element into a few simply formed parts.

A tenth aspect of the invention is an apparatus according to the fourth aspect, wherein divided parts being apart from one another, are tapered toward a gap. With the invention, since the line of the magnetic field can be densely generated on the outer side of the nozzle near the gap, a strong magnetic field can be applied to the nozzle. The tapered form implies for example, a truncated cone.

An eleventh aspect of the invention, is an apparatus according to the fifth aspect, wherein the pair of projections project from the opening edge of the through section of one of the magnetic plates to the other magnetic plate in a direction of insertion of the nozzle opposite to one another, and each tip of the projections is apart from the opposite surface at a first interval, and the tips of the projections are apart from one another separated from the nozzle at a second interval shorter than the first interval, in such a manner that the tips have opposite polarities, respectively.

The reason that the second interval is formed so as to be shorter than the first interval is so that the lines of the magnetic force can densely pass between the projections which are apart at the second interval.

A twelfth aspect of the invention is an apparatus according to the third aspect, wherein each through section of the magnetic force device comprises a separate hole in which the nozzle is inserted in a way that the outer surface of the nozzle can come in contact with or approach to the nozzle outer member, and an insert-withdraw hole mounted adjacent to the separate hole and having an opening larger than that of the separate hole so that the nozzle can horizontally move to and from the separate hole and can be withdrawn and inserted at the insert-withdraw hole.

The present invention needs a moving mechanism which can horizontally move the nozzle between the separate hole and the insert-withdraw hole and can vertically move the nozzle at the insert-withdraw hole, relative to the magnetic force device, as a precondition. The reason why the insert-withdraw hole is provided in addition to the separate hole is as follows.

A liquid is necessarily stuck on the periphery of the lower part of the nozzle which touches with the liquid accommodated in the vessel. Since the nozzle outer member mounted in the separate hole approaches or touches the nozzle, the liquid stuck to the periphery of the lower part may stick to the nozzle outer member and stain the nozzle outer member in the case where the nozzle comprising a pipette tip is pulled up from the through section. Once that happens, the nozzle outer member is stained, the nozzle outer member stains newly inserted nozzles, and cross-contamination may occur. Therefore, the nozzle is inserted in or withdrawn out from the through section, through the insert-withdraw hole whose opening is larger than that of the separate hole, so that the nozzle does not touch other members.

A thirteenth aspect of the invention is an apparatus according to the twelfth aspect, wherein the nozzle comprises a small diameter section and a larger diameter section, the separate hole has an opening that only the small diameter section can be inserted in, and the insert-withdraw hole has an opening that the larger diameter section can be inserted in.

With the invention, in the case where the nozzle has a small diameter section and a larger diameter section, the insert-withdraw hole has an opening that can take insertion of the larger diameter section. Thus, the opening can take insertion of the larger diameter section. Consequently the insert-withdraw hole is not stained by the small diameter section which is mounted in the lower section and touches the liquid, and cross contamination can be prevented. Further, since even the larger diameter section can be withdrawn and inserted, the nozzle can be easily inserted and withdrawn.

A fourteenth aspect of the invention is an apparatus according to the first aspect, wherein the magnetic force device can apply and remove the magnetic force to and from the nozzle with remaining stationary near each nozzle exterior.

With the invention, a uniform strong magnetic field can be applied to each nozzle at point-blank range.

Besides, the coil of the magnetic force device may be made of a single wire. Therefore, since ports etc. need not be Mounted per coil, the structure of the circuits can be simplified. Furthermore, since the coil is not mounted on the nozzle, the nozzle can be disposed of.

A fifteenth aspect of the invention is an apparatus according to the first aspect, wherein the magnetic force device comprises an insulating device for preventing heat generated by magnetization or generation of a magnetic field, from being transmitted toward the nozzle. With the invention, detrimental influence of heat on the nozzles can be avoided. Conversely, in a special case the heat may be positively utilized for the process without the insulating device. The insulating device may be one included in the fifteenth aspect, one provided by a Peltier effect element, or one provided for insulation against the magnetic sources.

A sixteenth aspect of the invention is an apparatus according to the fifteenth aspect, comprising a ventilator for sending air to the magnetic force device or the neighborhood thereof. Thus, transmission of heat to the nozzle can be efficiently prevented.

A seventeenth aspect is an apparatus according to the second aspect, wherein the magnetic force device comprises plural magnetic sources, and plural segments defined so as to include the area spatially near each magnetic source, respectively. For example, belt-like magnetic segments having through sections capable of taking insertion of a column of nozzles selected from the nozzles arranged in a plane-like state, are arranged in the direction of the magnetic field and have the same number of rows as the nozzles.

Therefore, in the case of manufacturing such a magnetic force device that can process a fluid by using a vessel having a plurality of liquid containing parts, the magnetic force device can be manufactured by being divided and the production cost can be reduced. The magnetic field can be uniformly distributed and a strong magnetic field can be applied.

An eighteenth aspect of the invention is an apparatus according to the third aspect, wherein the magnetic force device comprises a magnetic source having a permanent magnet or an electromagnet, and a plank-like member made of magnetic material and magnetically connected to the electromagnet or capable of magnetically connecting to the permanent magnet, wherein the through sections are provided in the plank-like member and are capable of taking insertion of the nozzles. With the invention, a magnetic force device having a simple structure is provided. For instance, "the plank-like member" may be formed by piling up thin plates made of magnetic material in the direction of magnetic force. With the invention, since the lines of magnetic force can be generated in the direction of the surfaces of the thin plates, leakage of magnetization can be suppressed to the minimum, and a uniform magnetic field can be obtained. Further, the thin plates can be piled up in a stratified state so that the normal direction of the thin plates is vertical or horizontal.

A nineteenth aspect of the invention is an apparatus according to the eighteenth aspect, wherein the through holes of the magnetic force device comprise divided wall parts divided in the direction of the insertion of the nozzle in such a manner that divided wall parts are apart from one another and have opposite polarities by magnetization.

A twentieth aspect of the invention is an apparatus according to the nineteenth aspect, wherein the nozzles comprise a larger diameter section and a small diameter section, and the plank-like member of the magnetic force device comprises plural column-like members arranged apart from each other at intervals capable of taking insertion of the larger diameter section of the nozzle, and plural protrusions made of magnetic material that are projected oppositely from each column-like member, magnetized in a manner that has opposite polarity to each other and arranged apart from each other at intervals capable of taking insertion of the smaller diameter section of the nozzle, and are arranged along the column-like member at intervals capable of taking insertion of the larger diameter section of the nozzle, wherein opposite pointed ends of the protrusions correspond with the divided wall parts. With the invention, since each column-like member is apart from each other, the lines of magnetic force run through the narrow interval between the pointed ends of the opposite protrusions. Therefore, a strong magnetic force can be supplied to the nozzles.

A twenty first aspect of the invention is an apparatus according to the second aspect, wherein the magnetic force device comprises a plank-like member made of magnetic material, plural through holes capable of passing a fluid and mounted in the plank-like member, small diameter pipes communicating with the through holes and capable of being inserted into a vessel and mounted under the through holes, wherein the through holes and the small diameter pipes serve as the nozzles. With the invention, since the nozzle itself constitutes the magnetic force device, the number of the members can be reduced, the apparatus can be formed to be compact, and a strong magnetic field can be applied into the nozzles.

A twenty second aspect of the invention is an apparatus according to the first aspect, wherein the drawing/discharging device comprises a reservoir body comprising plural reservoirs for storing a drawn fluid and communicating with the nozzles, and an increasing/decreasing device for increasing and decreasing pressure within the reservoirs and the nozzles in a manner that draws or discharges the fluid. The "reservoirs" can store a fluid. It follows that the reservoirs can store not only a liquid, but also a gas such as air. Thus, a process can be executed in a state that an air layer can be formed between the drawn or discharging liquid and the increasing/decreasing device or, a cleaning liquid. The shape of the reservoirs may be for example, hole-like with a bottom, with no bottom, with a lid, or with no lid, or pipe-like, or vessel-like. Further, the reservoirs may be integrated with the nozzles or be separate from the nozzle.

Furthermore, the number of reservoirs need not be the same to that of the nozzles.

For example, plural nozzles may communicate with a single reservoir. In the case where the number of nozzles is the same to that of the reservoirs, each nozzle may communicate with each reservoir one to one. Further a part of plural nozzles may jointly communicate with a single reservoir, or plural reservoirs may jointly communicate with a single nozzle.

Furthermore, the reservoir body which is an assembly of reservoirs, may be not only a plank-like one provided with plural hole-like reservoirs, but may be one with plural pipe-like or vessel-like reservoirs, assembled in a bundle.

With the invention, plural reservoirs can be simply manufactured in an integrated state by for example, piercing plural pits in the plank.

Moreover, the pressure may be increased and decreased by raising and lowering a sliding body as described in the fifteenth aspect. Further, the reservoir may have an expandable bellow mounted in a part of the side thereof and an opening connecting to the nozzle in a lower side thereof. The increasing/decreasing device may be a pressing device which presses the reservoirs and release the pressing of the reservoirs.

Furthermore, the increasing/decreasing device may comprise an inserting body which is made of an elastic solid at least partially, which can be inserted into the reservoirs by deformation and cover the top of the reservoirs, and a pressing device for pressing the inserting body for compressing the inside of the reservoir and releasing pressing thereof. Further, the reservoir may have a diaphragm and an opening mounted in the lower side thereof for connecting with the nozzle, and the increasing/decreasing device may be a pressing device for pressing the diaphragm and releasing pressing thereof.

A twenty-third aspect of the invention is an apparatus according to the twenty-second aspect, wherein the increasing/decreasing device comprises a sliding body capable of moving vertically to and from the reservoir body, and sliding projections projecting downward from the sliding body and capable of sliding through the nozzle in such a manner that the pressure within the reservoirs or nozzles increases or decreases.

With the invention, the apparatus has a simple construction. A fluid can be easily drawn or discharged with the same conditions for time, capacity and timing etc., all together, by moving the sliding body having plural sliding projections, to and from the reservoir body vertically.

A twenty-fourth aspect of the invention is an apparatus according to the twenty-third aspect, wherein the sliding projections are formed to have a two-step structure comprising a larger diameter section capable of sliding through the reservoir formed to be pit-like, and a smaller diameter section capable of extending along the axes of the larger diameter section and sliding through the nozzle communicating with the reservoir.

With the invention, when a relatively large amount of fluid is handled, drawing or discharging is executed by moving the sliding projections vertically in a state with the tip of the small diameter section and the tip of the larger diameter section fixed and aligned. On the other hand, when a relatively minute amount of fluid is handled, first, the sliding projections are moved vertically in a state with the tips of the small diameter section and the larger diameter section fixed and aligned. When the tips of the sliding projections stick to the lower part of the reservoir, drawing or discharging is executed by sliding only the small diameter section through the nozzle, vertically.

Thus, minute amounts of fluid as well as a relatively large amount of fluid can be processed at high precision. Therefore, an apparatus with reliability and diversity can be provided.

With the invention, residual liquid or remnants such as magnetic substances or particles remaining in the nozzles can be surely and efficiently discharged. Therefore the process for a fluid can be reliably executed.

Further, since the nozzles can be recycled by completely cleaning the nozzle with a cleaning liquid, cost for the process can be reduced in comparison to the case of using disposable nozzles or reservoirs. Here, though the sliding projection is formed to be two-steps, if necessary, the sliding projection may be formed to be multi-steps.

A twenty-fifth aspect of the invention is an apparatus according to the twenty-second aspect, wherein the nozzles comprise a tip capable of being mounted to and dismounted from the drawing/discharging device.

With the invention, cross contamination can be surely avoided without cleaning the nozzle. Therefore, since drawing and discharging can be executed through an air layer formed within the reservoir, the process can be efficiently executed, without cleaning.

A twenty-sixth aspect of the invention is an apparatus according to the twenty-fifth aspect, comprising a pushing body having pushing pipes inserted from the upper side of the reservoirs into the reservoirs and capable of pushing the nozzles out of the reservoirs, wherein the nozzles are detachably mounted to the reservoirs while being inserted from the lower side of the reservoirs, and the increasing/decreasing device comprises a sliding body having plural sliding projections projecting downward, capable of sliding through the pushing pipe and capable of moving vertically to and from the reservoirs respectively, in a manner that the pressure within the reservoirs or nozzles can be increased or decreased.

With the invention, since the process can be executed in such a manner that drawing or discharging liquid is apart from the pushing body by an air layer, cross contamination can be surely prevented by exchanging only the nozzle. Furthermore, the nozzles are detachably mounted to the reservoirs, and the nozzles can be easily dismounted all together by moving the pushing body downward.

A twenty-seventh aspect is an apparatus according to the twenty-fifth aspect, wherein the nozzles are detachably mounted to the lower part of pit-like reservoirs and are inserted to a predetermined depth in the pit-like reservoirs, the sliding projections can slide to a depth of the installation depth of the nozzles in the reservoirs, and a projecting lip part is projected from the outer side of the nozzles exposed under the magnetic force device for mounting and dismounting, and a stroke-down plate provided with plural small hole parts with respective diameters larger than that of the nozzles and smaller than that of the lip parts is mounted between the magnetic force device and , the lip parts in a way that the hole parts take insertion of the nozzles and the nozzles can be detached by moving the stroke-down plate down.

With the invention, the nozzle can be easily detached by moving the stroke-down plate downwards. Further, the sliding, projections do not touch with the liquid, and cross contamination can be surely prevented while drawing and discharging the liquid etc. through the medium of the air layer within the reservoir.

A twenty-eighth aspect is an apparatus according to the twenty-third aspect, wherein an inner wall of the upper part of the reservoir is formed to be cylindrical, and that of the lower part of the reservoir is formed to be funnel-shaped and is connected with the nozzles. With the invention, since the lower part thereof is formed to be funnel-shaped and the tip of the sliding projections is formed so as to fit closely with the lower part of the reservoir, residual liquid can be surely avoided and a process can be reliably executed.

A twenty-ninth aspect of the invention is an apparatus according to the first aspect, wherein the magnetic force device is constructed to be able to relatively move to and from the drawing/discharging device or the nozzle. With the invention, since the magnetic force device is constructed as mentioned above, the magnetic force device can surely apply and remove the magnetic force. For example, after the magnetic force by the magnetic force device is removed, the process for discharging etc. is executed by moving the drawing/discharging device upwards and keeping the nozzle away from the magnetic force device so that the effect by residual magnetization can be reduced. Furthermore, in the case where the nozzle is detachably mounted to the drawing/discharging device, the nozzle can be easily detached.

A thirtieth aspect of the invention is an apparatus according to the twenty second aspect wherein a cleaning liquid can be poured into each reservoir from the top or side of the reservoir body.

The invention is embodied, for example, by connecting the reservoir to the vessel accommodating the cleaning liquid by mounting a change-over valve at some midpoint of a hose connecting between the reservoir body and the increasing/decreasing device, or by providing a passage communicating with the vessel accommodating the cleaning liquid, in the side wall of the reservoir body. Further, it may be embodied by detaching the sliding projections and inserting a cleaning liquid pipe, instead of the detached sliding projections, or by providing a pipe for pouring a cleaning liquid into the sliding projection per se and so on. With the invention, since the vessel accommodating the cleaning liquid need not be transported, the process can be efficiently executed.

A thirty first aspect of the invention is an apparatus according to the first aspect, comprising a light measuring device for receiving light from all the vessels or plural liquid containing parts simultaneously or all together and measuring the strength of the light or processing the light as an image in order to measure a state of light emission.

With the invention, measuring light emission can be easily, efficiently and reliably executed, in comparison to the case where measurement of liquid emission is executed by moving a PMT device per liquid containing part or by mounting a PMT device for each liquid containing part.

A thirty second aspect of the invention is an apparatus according to the thirty first aspect, wherein the light measuring device comprises plural receiving components mounted at places corresponding to the liquid containing parts and having the same number as that of the liquid containing parts, and shading fences mounted between neighboring receiving components for preventing light from entering to other than the corresponding liquid containing part.

A thirty third aspect of the invention is a magnetic apparatus comprising, plural outer members capable of being mounted to and dismounted from a pipette device having a drawing/discharging device for drawing and discharging a liquid, and plural nozzles through the interior of which liquid passes due to the drawing and discharging, one or more vessels arranged with plural liquid containing parts, or column clusters arranged by plural columns, and capable of being brought into contact with or approaching to each outer surface of each nozzle, each liquid containing part or each column, while being mounted to the pipette device, the vessel or the column cluster, and a magnetic force device for applying a magnetic force to or removing the magnetic force from each nozzle, each liquid containing part or each column in a state with remaining stationary, by magnetizing and demagnetizing the outer members or by generating or extinguishing the magnetic field with coils which are mounted around each nozzle, each liquid containing part or each column while fitting to the pipette device, the vessel or the column cluster.

"Column" means a liquid containing part comprising at least a mechanism capable of discharging a liquid such as a valve, and another mechanism for selectively drawing a liquid such as a valve.

With the invention, since the magnetic device can be mounted onto a pipette device, a vessel or a column cluster, and the process for target substances combined with the magnetic particles can be accumulated by utilizing the already existing pipette device, vessel or column cluster, and be utilized, the process can be executed at low cost.

A thirty fourth aspect of the invention is a magnetic apparatus according to the thirty third aspect, wherein the magnetic force device is the magnetic force device according to any one of the third to twenty first aspects applied to the nozzles, liquid containing parts or columns.

With the invention, the magnetic apparatus is applied to not only the pipette device arranged with plural nozzles but also to a vessel arranged with plural liquid containing parts or a column cluster arranged with plural columns. In the latter two cases, since the magnetic force device is applied to the liquid containing parts or columns, the diameter of each through section etc. is changed according to the liquid containing part or column.

A thirty fifth aspect of the invention, is an apparatus according to any one of the first to the thirty fourth aspects, wherein plural nozzles, plural through sections, plural reservoirs, plural sliding projections, plural hole parts, plural pushing pipes, plural liquid containing parts of the vessel, plural columns of the column cluster or plural receiving components are arranged in a plane-like state with a predetermined periodicity or a predetermined symmetry such as plural row-shaped, matrix-shaped, annular ring-shaped, polygonally, or radially.

"Matrix-shaped" means a state where plural elements are arranged at least in two directions (row direction and column direction) or in parallel, in a plane-like state. "Row" means the arrangement in the row direction, while "column" means the arrangement in the column direction. The row direction and the column direction need not always cross at 90°. These directions may cross obliquely. Further, these plural elements may be arranged in a dense state while being alternately shifted by one between the neighboring rows or columns.

With the invention, integration can be facilitated. Since plural elements are arranged with a predetermined periodicity or symmetry, rotating movement and transposed movement (rows and columns are exchanged one with another) are possible by the pipette device according to the symmetry, and the control of movement and standardization are facilitated.

A thirty sixth aspect of the invention, is an apparatus comprising a reservoir body provided with plural pit-like reservoirs for storing drawn liquid arranged in a matrix, a sliding body with jutting plural sliding projections sliding through the reservoirs and capable of moving vertically to and from the reservoir body, plural nozzles attached to the lower parts of the reservoirs and capable of passing the liquid therethrough, a magnetic force device capable of magnetization and demagnetization having plural through sections in which is inserted each nozzle and having a wall part in contact with or near the outer side surface of the nozzle, with the nozzles inserted thereinto, wherein each wall part has two divided wall parts being apart from one another in such a manner that the divided wall parts have opposite polarities by magnetization, respectively.

A thirty seventh aspect of the invention is an apparatus according to any one of the first to thirty second aspects, the thirty fifth aspect, and the thirty sixth aspect, comprising a driving mechanism for driving the drawing/discharging device to draw and discharge, a magnetic controller for controlling the magnetic force of the magnetic force device, a transfer mechanism for transferring between vessels placed outside the pipette device, and the drawing/discharging device and the magnetic force device or between the drawing/discharging device and the nozzles and the magnetic force device, and an integrated process controller for controlling an integrated process of magnetic particles by controlling at least the driving mechanism, the magnetic controller, and the transferring mechanism according to instructions.

"Transferring" implies horizontal transferring, vertical transferring or rotational transferring. "Rotational transferring" includes transferring by transposition.

With the invention, since the driving mechanism, the magnetic controller and the transferring mechanism can be handled by a single controller in a coordinated fashion, efficient, diverse and reliable control can be executed.

A thirty eighth aspect of the invention is an apparatus according to the thirty seventh aspect, wherein the controller controls an insulating device such as a ventilator, the pouring of cleaning liquid, a light measuring device, and data analysis, data disposition, or data output.

A thirty ninth aspect of the invention is an apparatus according to the thirty seventh aspect, wherein the controller controls either the strength, direction, or application time of the magnetic force, or magnetic patterns obtained from various combinations of strength, direction and time, according to the contents, conditions or objects of a target controlling step, the fluid, substances such as reagents, kinds, shape, quantity, combining state, or size of the magnetic particles, the pressure, the fluid velocity, the number of times of drawing/discharging, processes of transferring, agitation, cleaning, separation, removal extraction, reaction, clarification, concentration, dilution, recovery, isolation, or resuspension, external surroundings such as temperature, structure of the apparatus, materials or size of the apparatus, progress or schedule of magnetic control, degree of the residual magnetization, or instructions from the outside.

The degree of residual magnetization is obtained by measuring the magnetization with a coil of the magnetic force detecting device mounted near the apparatus or nozzle thereof. The measured results are fed back to the magnetic force device for use in control of the magnetic force device.

With the invention, according to the contents of the steps etc., precise, efficient, and reliable processes can be executed by controlling delicately to vary the strength, direction, or time for applying the magnetic field or the magnetic pattern obtained from a combination of the strength, direction, or time.

A fortieth aspect of the invention is an apparatus according to the thirty ninth aspect, wherein the controller controls in such a manner that the direction of the magnetization controlled by the magnetic controller is alternately reversed each time the magnetization is paused by demagnetization.

Therefore, since the direction of the magnetization in the wall parts etc. of the magnetic force device is alternately reversed, residual magnetization is offset, and magnetic noise due to the residual magnetization is reduced, even if the wall part is made of a para-magnet such as iron.

A forty first aspect of the invention is an apparatus according to the thirty ninth aspect, wherein the magnetic controller controls in such a manner that the direction of the magnetization is reversed with a strength or a driving time corresponding to that of the non-reversed magnetization, when changing a magnetized state to a demagnetized state.

Thus, generation of residual magnetization is prevented or the affect of the residual magnetization is reduced by generating magnetization that can offset the residual magnetization generated by the magnetization, according to the extent of the magnetization immediately before demagnetization.

A forty second aspect of the invention is a method comprising the steps of: drawing or discharging all together a fluid to or from a vessel comprising plural liquid containing parts by a drawing/discharging device mounted in the apparatus for an integrated process according to any one of the first to thirty second aspects, or the thirty fifth to forty first aspects, and applying the magnetic force to or removing the magnetic force from the nozzles in a state that remains stationary near the nozzles exterior, by generating or extinguishing the magnetic field with magnetization and demagnetization of the nozzle outer members mounted in contact with or near the periphery of the nozzles or a part of the nozzles, or by generation or extinguishing the magnetic field with a coil wound around the periphery of each nozzle.

A forty third aspect of the invention is a method according to the forty second aspect comprising further the steps of: mixing magnetic particles and the target substances by drawing and discharging all together with the apparatus for an integrated process, to make a suspension incorporating the magnetic particles combined with the target substances in plural liquid containing parts of the vessel, processing for separation by adhesion to the inner walls of the nozzles, elimination from the inner walls, transferring, resuspension, agitation, dissociation, extraction, reaction, clarification, concentration, dilution, recovery, isolation, or cleaning of the magnetic particles combined with the target substances by applying the magnetic force to, or removing a predetermined magnetic force from magnetic particles combined with the target substances within the nozzles, while drawing and discharging the liquid.

"Dissociation" means removal of magnetic particles from the target substance, and "extraction" means the removal of the magnetic particles combined with the target substance, or only the target substance.

A forty forth aspect of the invention is a method according to the forty second aspect or the forty third aspect, further comprising a step for measuring all together light emission of the liquid accommodated in each liquid containing part and processed by the apparatus for an integrated process.

A forty fifth aspect of the invention is a method according to the forty third aspect, wherein the apparatus for an integrated process for magnetic particles whose plural nozzles are arranged in a matrix is used, and the processing for the transferring step comprises a transposed moving step for moving in such a manner that rows and columns of the nozzles of the apparatus for an integrated process or the liquid containing parts of the vessel, are exchanged, or a horizontal moving step for transferring in such a manner that rows and columns are not exchanged.

With the invention, combinations of a variety of substances can be efficiently and reliably generated all together by the transposed moving and the horizontal moving or a repetition of these movements.

A forty sixth aspect of the invention is a method of making any combined substances in carriers by arbitrarily combining with plural elements of substances, comprising the steps of: dispensing peach liquid incorporating each element of substances into one or more groups of containing parts arranged by plural containing parts in a matrix in which the containing parts accommodating said carriers are arranged in rows or columns having a predetermined number width in a way so as to be included in the matrix, according to the structure of the specified combined substances or the utilized kinds of containing parts, and mixing the dispensed elements of substances into the group of the containing parts accommodating the carriers, with the elements of substances arranged in rows or columns having a predetermined number width, in such a manner that row-like or column-like arrangements of the dispensed elements of substances are positioned against row-like or column-like arrangements of the elements of substances in a state of transposition or non-transposition.

"Element of substances" implies for example, genetic substances such as DNA or RNA etc., or amino acids, "combined substances" implies for example, a variety of compounds such as DNA, RNA or peptides etc.

The invention may apply to not only the process using the magnetic particles as carriers, but also the process using the non-magnetic particles as polymer carriers. The vessel may have the liquid containing parts arranged in a matrix and may have a capturing function by mounting for example, a filter. Instead of vessels, columns arranged in a matrix and having a capturing function, may be used. The carriers may be solid carriers which are fixed to the surface of the liquid containing parts arranged in a matrix. Further, instead of having a capturing function in the vessel, a pipette device for drawing and discharging liquid, may have a capturing function by mounting a magnetic force device.

With the invention, combined substances of various structures can be integratedly generated by mixing the liquid incorporating elements of substances in such a manner that the row-like or column-like arrangements of liquids are transposed or non-transposed in a matrix. The invention may apply to combinatorial synthesis. The function for capturing the magnetic particles is embodied by the magnetic force device according to the thirty-third or the thirty-forth aspect.

A forty-seventh aspect of the invention, is a method according to the forty-sixth aspect for when the containing parts are liquid containing parts provided in a vessel and arranged in a matrix, comprising the steps of: disposing the carriers in the liquid containing parts of one of the one or more vessels, dispensing each liquid incorporating each element of substances into one or more vessels including vessels in which the carriers are disposed, in a state with rows or columns having a predetermined number width, according to the structure of the combined substances, and mixing each liquid incorporating each element of substances and disposed in a state with rows or columns having a predetermined number width in the other one or more vessels, with the dispensed liquid incorporating the elements of substances into the vessels in which the carriers are disposed, in such a manner that row-like or column-like arrangements of the dispensed elements of substances are positioned against row-like or column-like arrangements of the elements of substances in a state of transposition or non-transposition.

The invention may apply to the case where the magnetic particles are used as carriers (in the case including the case where a capturing carrier function is provided for the vessels, or a capturing carrier function is provided for the pipette device), the carriers are solid carriers fixed in the liquid containing parts, or the carriers are non-magnetic particles and the carrier capturing member is mounted in the vessels. The capture of the magnetic particles can be executed by the magnetic force device according to the thirty-third or the thirty-forth aspect.

A forty-eighth aspect of the invention is a method according to the forty-sixth aspect, for when the containing parts are plural columns arranged in a matrix and having a function for capturing carriers comprising the steps of, disposing the carriers to each column having a capturing function, dispensing each liquid incorporating each element of substances into the columns arranged in a matrix in a state with rows or columns having a predetermined number width, according to the structure of the specified combining substances, mixing the dispensed elements of substances into the group of the group of the columns accommodating the carriers, with the elements of substances arranged in rows or columns having a predetermined number width, in such a manner that row-like or column-like arrangements of the dispensed elements of substances are positioned against the row-like or column-like arrangements of the elements of substances in a state of transposition or non-transposition.

The invention may apply to the case where the carriers are magnetic particles or non-magnetic particles, or solid carriers. In the case where the carriers are magnetic particles, the capturing carrier function may be embodied by a magnetic field. In the case where the carriers are non-magnetic particles, the capturing carrier function may be embodied by a filter. In the case of solid carriers, the solid phase per se has the capturing function. The capturing magnetic particles function may be embodied by the magnetic force device according to the thirty-third aspect or the thirty-forth aspect.

BRIEF DESCRIPTION OF THE DRAWINGS

FIG. 11 is a perspective view showing a nozzle according to the sixth embodiment of the present invention.

FIG. 12 is a view showing a concept for a process according to a seventh embodiment of the present invention.

FIG. 13 is a view showing a magnetic force device according to any one of eighth to twelfth embodiments of the present invention.

FIG. 16 is a view showing another magnetic force device according to the fourteenth embodiment of the present invention.

DETAILED DESCRIPTION OF THE PREFERRED EMBODIMENTS

FIRST EMBODIMENT

An apparatus for an integrated process for magnetic particles (referred to hereunder as "an apparatus") according to a first embodiment of the present invention is described on the basis of FIGS. 1 to 4.

Figure 1:
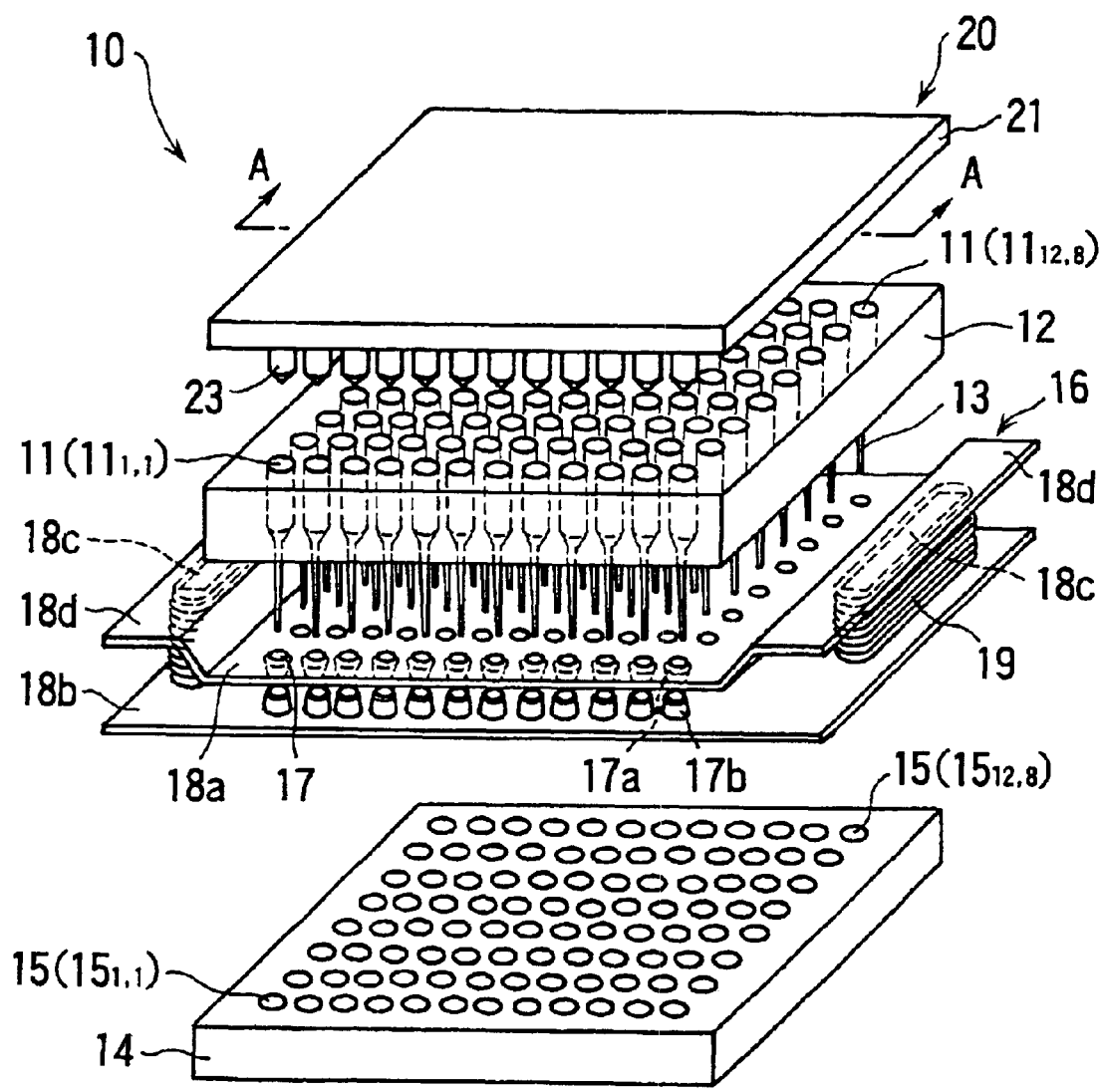
FIG. 1 is a separated perspective view showing an apparatus for an integrated process according to a first embodiment of the present invention.
Figure 2:
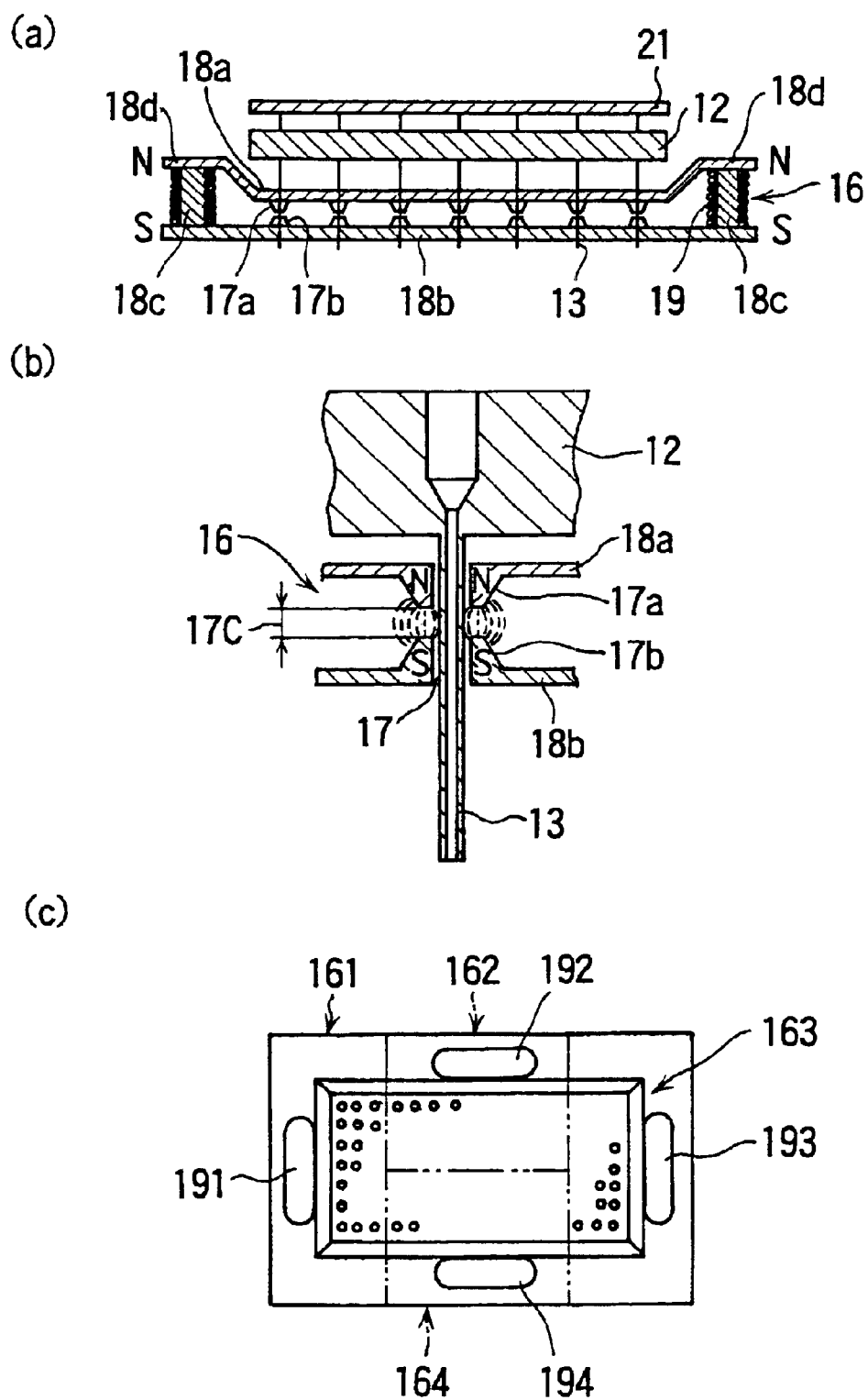
FIG. 2 is a view showing a magnetic force device according to a first embodiment of the present invention.

As shown in FIG. 1, the apparatus 10 comprises a plank-like reservoir body 12 where plural (96 in this example) cylinders 11 ($11_{1,1}$~$11_{12,8}$) serving as pit-like reservoirs are pierced and arranged, in a plane state (in a matrix having 12 rows×8 columns in this example).

Plural nozzles 13 communicating with each cylinder 11 are mounted under the reservoir body 12, and formed integral with the reservoir body 12, in a way that the nozzles 13 project downwards from the reservoir body 12. The length and the diameter of the nozzles 13 are determined so that the plural nozzles 13 can be inserted into plural hole-like liquid containing parts (holes) 15 ($15_{1,1}$~$15_{12,8}$) provided in a vessel 14 placed under and outside the apparatus 10, and having a capacity large enough to store the liquid of the liquid containing parts 15.

Further a moving mechanism (not shown) is mounted in such a manner that either or both of the reservoir body 12 and a stage on which the vessel 14 is placed can move vertically, horizontally and rotatatively relative to each other. For example, a link mechanism, a cam mechanism, a ball screw mechanism, a stepping motor or a DC motor is utilized as the above moving mechanism.

A magnetic force device 16 capable of applying and removing a magnetic force to and from within each nozzle 13 respectively in such a manner that the neighborhood of the outside of each nozzle 13 remains stationary, is mounted under the reservoir body 12 and above the vessels 14.

The magnetic force device 16 comprises an upper plate 18a and a lower plate 18b which are made of magnetic material and are mounted oppositely at a predetermined interval, and are capable of being magnetized and demagnetized.

The two plates 18a, 18b are supported and fixed by support pillars 18c which are sandwiched by edges 18d thereof. A coil 19 is mounted in such a manner that a conductive wire is wound around the side of the support pillar 18c. The coil 19 connects with a switch and power source which are not shown in the drawings, and constitutes an electromagnet capable of generating and extinguishing the magnetic field. It is preferable to form steps between the edges 18d and the upper plate 18a so that the turn number of the coil 19 can be larger.

On the surfaces of the upper plate 18a and the lower plate 18b which face one another, plural projections 17a, 17b made of magnetic material are formed to be tapered off in a substantially truncated cone and are mounted separately or as one piece to each plate 18a, 18b in such a manner that they project at the locations corresponding to the nozzles, and are arranged in a matrix.

The tips of the projections 17a, 17b are mounted so as to be apart from one another without contact.

At the projections 17a, 17b, through sections 17 capable of taking insertion of the nozzles 13 respectively, are mounted in such a manner that they penetrate the upper plate 18a, the lower plate 18b and the projections 17a, 17b vertically. Each wall part of the through sections 117 is capable of being magnetized and demagnetized, and is in contact with or near the upper part or intermediate part of the outer side of the inserted nozzle 13. Due to the structure of the magnetic force device 16, a magnetic force can be applied to or removed from the nozzle 13 in a state with the neighborhood of the outside of each nozzle 13 remaining stationary, by conducting or cutting off power to the coil 19 serving as a magnetic source. Here, movement of the magnetic force device 16 as well as the reservoir body 12 is controlled together by the moving mechanism for the reservoir body 12. The magnetic force device 16 may be mounted in such a manner that it can be dismounted from the reservoir body 12.

A sliding body 20 is mounted above the reservoir body 12, and is capable of moving vertically relative to the reservoir body 12. The sliding body 20 comprises a base plate 21, plural plungers 23 for sliding in the cylinders 11 and projecting downward from the base plate 21 and arranged in a matrix and serving as sliding projections. The entire length of the plungers 23 is at least the same as or longer than depth of the cylinders 11.

The sliding body 20 comprises a mechanism (not shown in drawings), for moving vertically relative to the reservoir body 12. Such a mechanism may be for example, a link mechanism, a cam mechanism, a ball screw mechanism, a stepping motor, or a DC motor etc. Here, the vessel 14 is driven to move by a moving mechanism (not shown in the drawings) in relation to the reservoir body 12, or by a stage on which the vessel 14 is placed.

The apparatus 10 including such mechanisms may be installed into a frame body or a case body (not shown in the drawings). The frame body or the case body may have a transfer mechanism for the vessels. Furthermore, the nozzles 13 may be formed to be separate from the reservoir body 12 and fitted to the lower part of the reservoir body 12, instead of being integrated with the reservoir body 12. It is preferable that the reservoir body 12, the nozzles 13 and the vessel 14 are formed to be transparent or translucent so that the interior thereof can be seen therethrough. Moreover, O-rings may be mounted around the interior circumference of the upper part of the cylinders 11 for preventing leakage of liquid.

FIG. 2(a) is a schematic side view showing the whole apparatus according to the present embodiment.

The magnetic material used for the upper plate 18a and the lower plate 18b etc. is a para-magnet such as iron (or a ferro-magnet with a temperature higher than the Curie temperature). Alternatively, an ideal magnetic force device free of residual magnetization can be obtained by using a super para-magnet, which is the aggregate of minute particles of ferro-magnet or anti-ferro-magnet materials (NiO, $Fe_3O_4$, $Cr_2O_3$ etc.). The appropriate magnetic material is one such as Fe—Co alloy (49Co—2V—Fe) having a high saturation magnetic flux density and a high magnetic permeability.

As shown in FIG. 2(b), when the magnetic field is generated by conduction in the coil 19 of the magnetic force device 16, the upper plate 18a is magnetized so as to have N polarity (or S polarity), and the lower plate 18b is magnetized so as to have S polarity (or N polarity). Therefore, each wall part of the through sections being apart from one another can have opposite polarities respectively. Further, the nearest location between the upper plate 18a and the lower plate 18b is a gap 17c between the tips of the projections 17a, 17b.

Therefore, since the heaviest concentration of the leakage of the lines of magnetic force is between the tips of the projections 17a, 17b, a strong magnetic field can be exerted on the nozzle 13, as shown in FIG. 2(b).

Furthermore, FIG. 2(c) shows another example of a magnetic force device. For instance, the magnetic force device may comprise an upper plate and a lower plate, one or more (four in this example) pillars sandwiched between the plates and one or more (four in this example) electromagnets comprising coils 191–194 having a wire wound around each pillar and connected with a switch and a power source (not shown in the drawings).

Further, in this embodiment, the magnetic force device may be divided into four segments 161, 162, 163, 164 in such a manner that the coils 191–194 can be included in each segment, respectively. Thus since a uniform magnetic field can be applied over a vide range, the apparatus can process a vessel having plural liquid containing parts.

Figure 3:
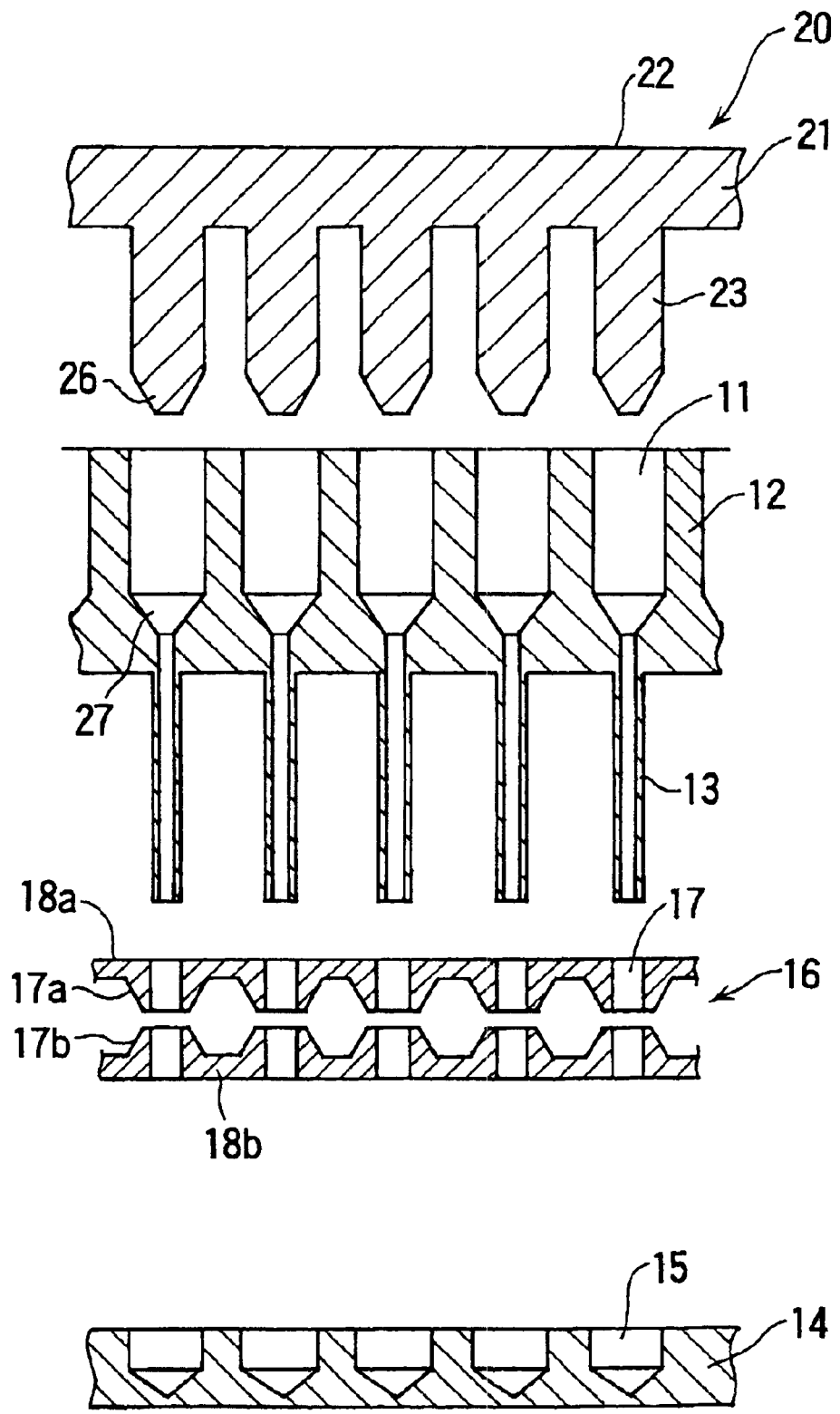
FIG. 3 is a cross-sectional view taken on line A—A in FIG. 1, showing an apparatus for an integrated process according to a first embodiment of the present invention.

FIG. 3 shows a cross-sectional view taken on line A—A in FIG. 1. As shown in this figure, the tips of the plungers 23 projecting from the sliding body 20, are formed in a conical shape with a downwardly disposed apex. Funnel parts 27 formed to be funnel-like are mounted in such a manner that the plungers 23 come in contact with the funnel parts 27 without a gap.

In the case of the measurement of light emission from the processed liquid accommodated in each liquid containing part 15 of the vessel 14, a light measuring device (not shown) in which light receiving components are arranged in a plane-like state, in a way to correspond to the location of each liquid containing part of the vessel, or light receiving components such as CCD elements are partitioned lattice-like is used.

Since the light emission as a whole can be collectively caught as a plane image and the analysis of the light emission can be executed without time lag, results having the same conditions in time and high precision can be obtained and the process can be swiftly and efficiently executed.

Figure 4:
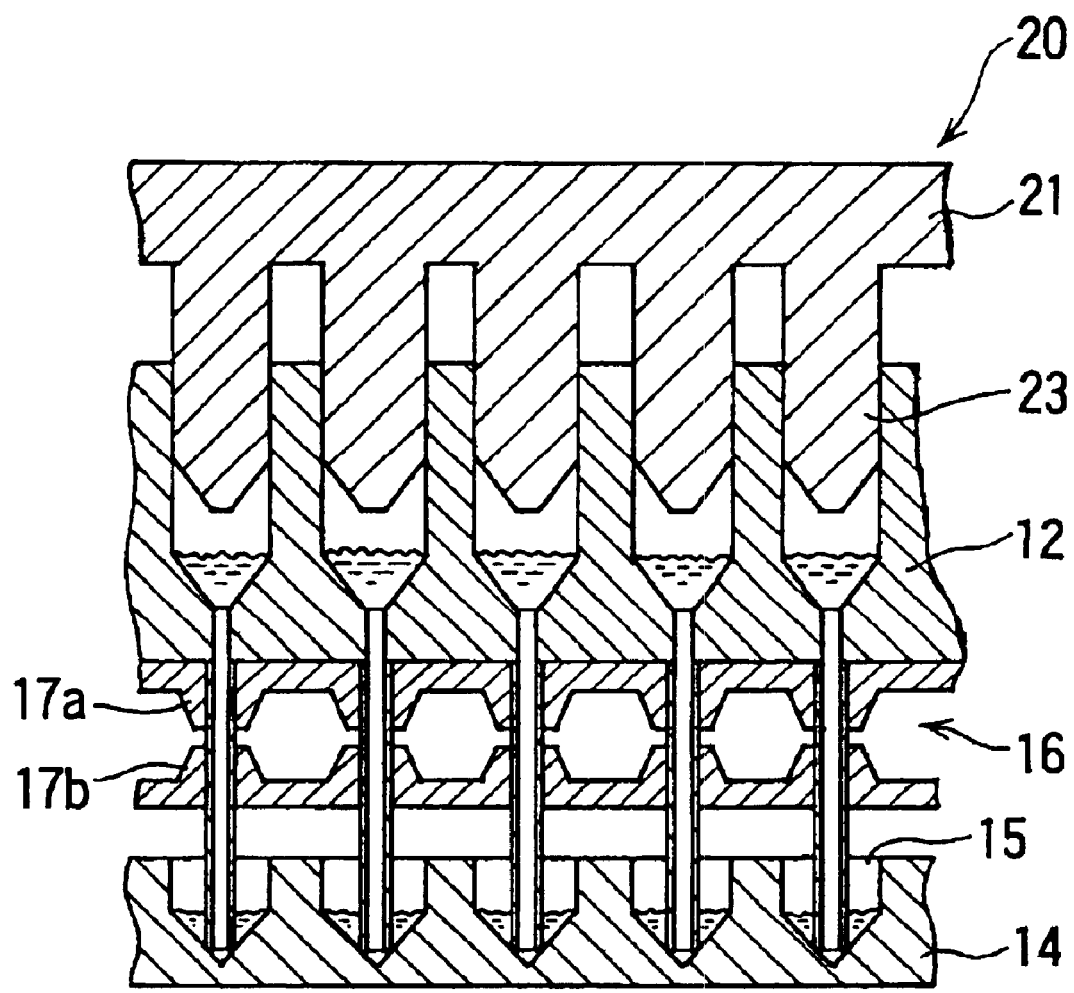
FIG. 4 is a cross-sectional view showing an assembled apparatus for an integrated process according to a first embodiment of the present invention.

FIG. 4 shows the assembled apparatus 10 according to the present embodiment put to actual use.

In order to use the apparatus 10 according to the present embodiment, a user instructs a controller (not shown). Then a nozzle head of the apparatus 10 or a stage moves a vessel (not shown) accommodating the liquid incorporating the magnetic particles, so that the nozzles 13 draw the suspension from the vessel collectively. Each nozzle 13 is positioned to each liquid containing part 15 of the vessel 14 corresponding to an object to be inspected or processed in a manner that the nozzle is located opposite the liquid containing part.

Then the suspension is discharged, to the specimens accommodated in the liquid containing parts and is collectively mixed with the specimens. Thus, each of the magnetic particles can be combined with the target substances contained in the specimens. When the nozzle is withdrawn again, the electromagnet is driven by passing current through the coil 19, and the upper plate 18a and the lower plate 18b are magnetized to have N polarity (or S polarity) and S polarity (on N polarity) respectively. Then the lines of magnetic force are generated along the upper plate 18a, the lower plate 18b and the pairs of projections 17a, 17b, and leak out from the gaps 17c.

Therefore, the magnetic field can be applied to the nozzles 13 placed near the gaps 17c. The magnetic particles combined with the target substances by adsorption or reaction with the substances coated with the magnetic particles or by direct adsorption to the surface of the magnetic particles, adhere to and are held to the inner wall of the nozzles 13. Thereafter, the residual liquid is discharged by lowering the sliding body 20, while applying the magnetic field. Thus only the magnetic particles combined with the target substances can be separated within the nozzles 13. Then the apparatus 10 per se or vessel on a stage moves, so that each nozzle 13 is positioned with respect to each liquid containing part accommodating the necessary reagents. Thereafter, drawing and discharging are repeated in a state with the magnetic field removed, and mixing with the reagents is executed by agitation in order to execute an other process.

The target substances are processed by executing the above steps or repeating the execution. When required, light emission is observed, the strength of the light is measured or processed as an image by a light measuring device (not shown), and the controller executes data processing of the results, and the results of measurement are displayed on a monitor screen, or are recorded in a memory device.

SECOND EMBODIMENT

Figure 5:
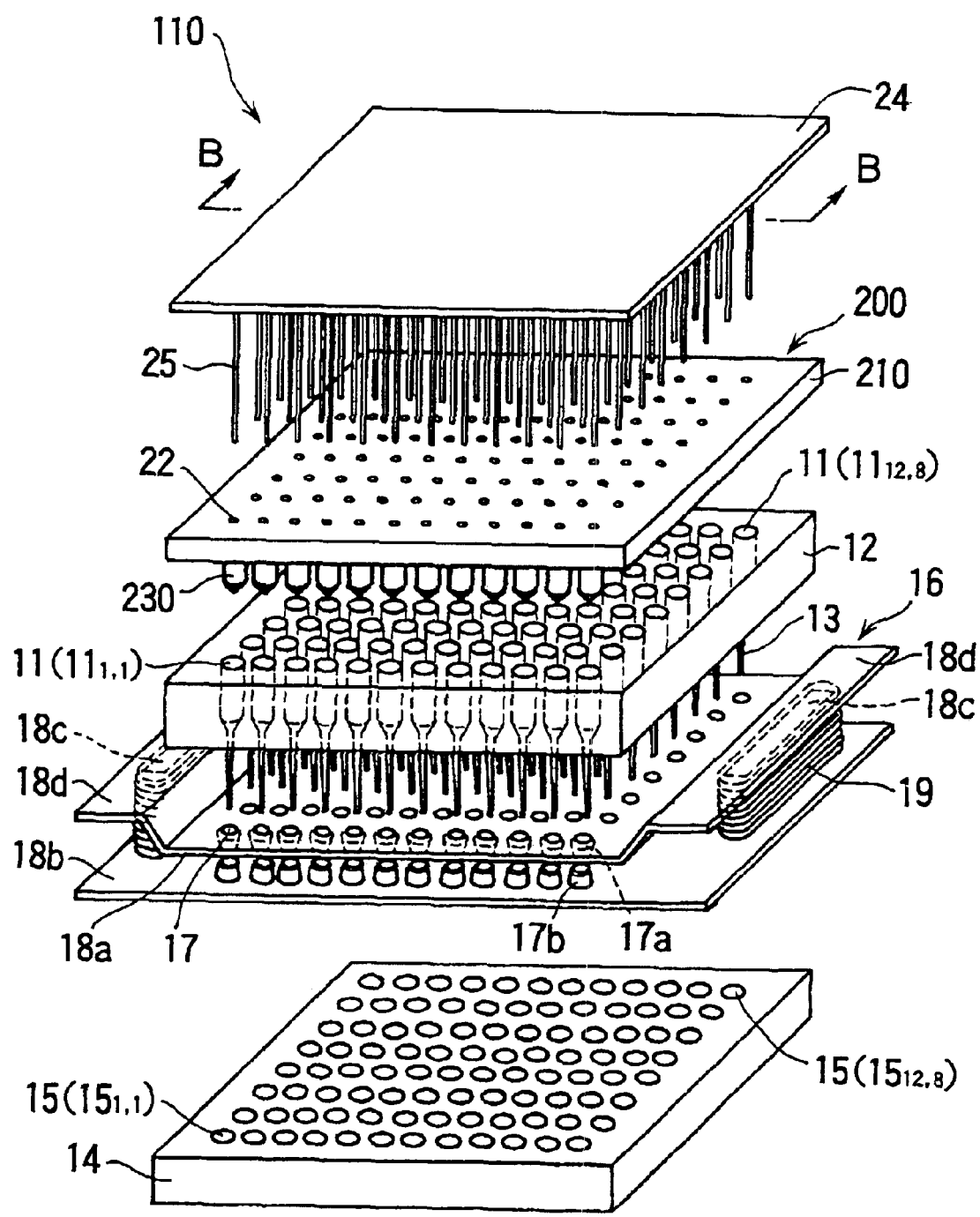
FIG. 5 is an exploded perspective view of an apparatus for an integrated process according to a second embodiment of the present invention.

Next, an apparatus according to a second embodiment is shown in FIG. 5.

In FIG. 5, like elements are given the same reference numerals as the first embodiment. The sliding body 200 comprises a base plate 210, and plural plungers 230 projecting downward from the base plate 210, arranged in a matrix, sliding through the cylinders 11 and capable of moving to and from the reservoir body 12 vertically, and serving as the larger diameter section of the sliding projections. Thin holes 22 penetrate the base plate 210 and the plungers 230 vertically. A minute sliding body 24 is mounted above the sliding body 200 with projecting downward plural thin rods 25 sliding through the thin holes 22 and the nozzles 13 and serving as the small diameter section, and capable of moving vertically to and from the sliding body 200.

The entire length of the thin rods 25 is at least the same as or longer than the entire depth of the thin holes 22 and the entire length of the nozzles 13.

Such minute quantities of liquid that are hard to handle by moving only the sliding body 200 vertically, can be handled and processed by moving the minute sliding body 24 vertically with high precision. Liquid and residual substances remaining in the nozzles 13 can be completely precluded.

Mechanisms (not shown) for vertical movement and horizontal movement are mounted on the sliding body 200 and the minute sliding body 24 respectively. Such mechanism may be for example, a link mechanism, a cam mechanism, a ball screw mechanism, a stepping motor, or a DC motor. These mechanism and the apparatus may be installed in a frame body or enclosed in a box (not shown).

Further, a transfer mechanism may be mounted in the frame body or the box body. Instead of being a single-piece construction, the nozzles 13 may be formed to be separate from the reservoir body 12. An O-ring may be mounted along the interior circumference of the upper part of the cylinder 11 for preventing leakage of liquid therefrom.

Figure 6:
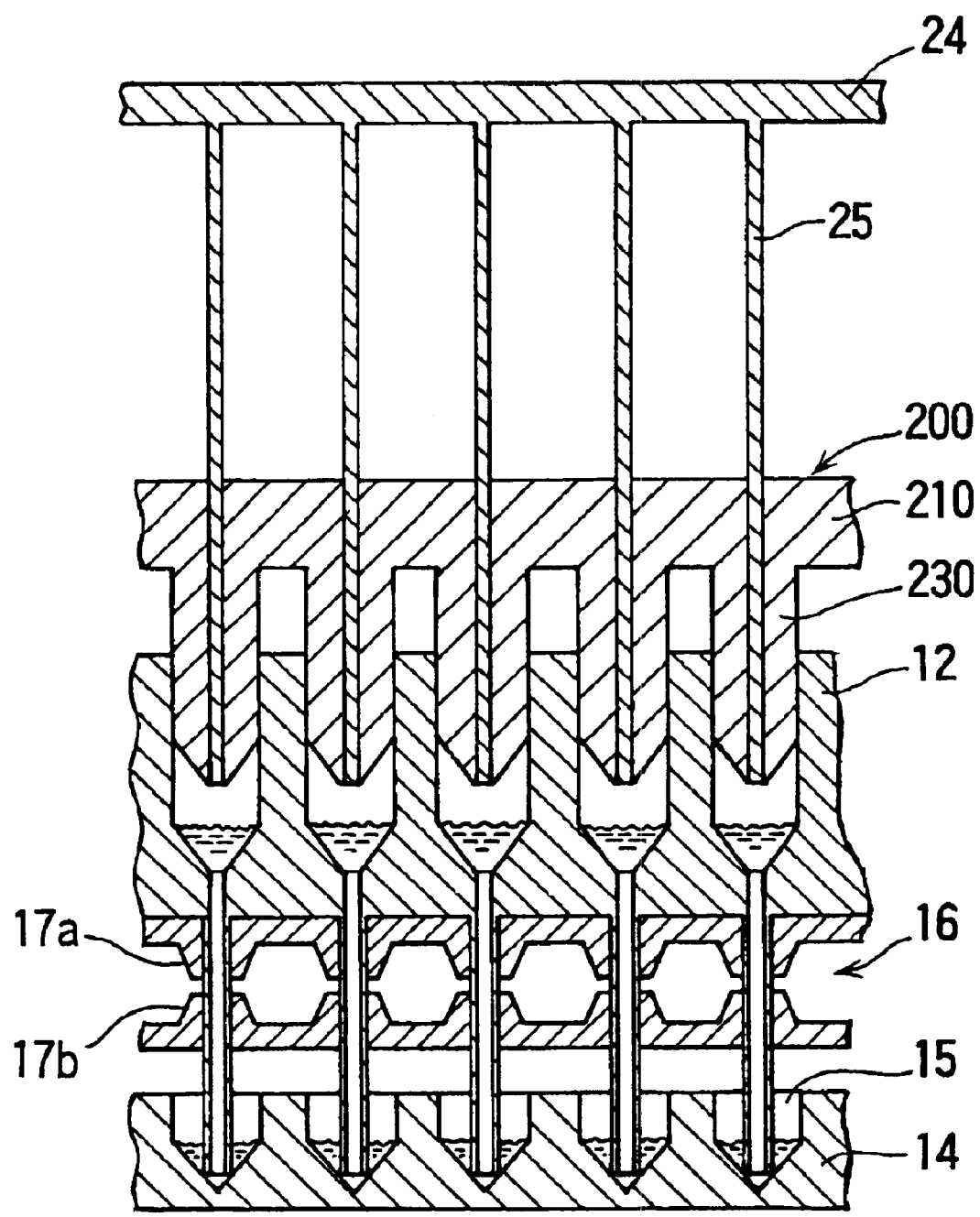
FIG. 6 is a cross-sectional assembled view taken on line B—B in FIG. 5, showing an apparatus for an integrated process according to the second embodiment of the present invention.

FIG. 6 shows a cross-sectional view taken on line B—B of FIG. 5 of the assembled apparatus 110 according to the present embodiment. In the case where a comparatively larger amount of liquid is processed, drawing and discharging are executed by sliding the sliding body 200 and the minute sliding body 24 vertically with the tip of the plunger 230 of the sliding body 200 and the tip of the thin rods 25 of the minute sliding body 24 coinciding.

On the other hand, in the case where a minute amount of fluid is drawn or discharged with high precision, the plungers 230 are lowered to the lowest ends of the cylinders 11 together with the sliding body 200, and only the thin rods 25 of the minute sliding body 24 are further allowed to slide through the nozzles 13 for drawing or discharging. Furthermore, the tips of the thin rods 25 can be moved up to the tips of the nozzles 13 or to penetrate through the nozzles 13 to the outside.

THIRD EMBODIMENT

Figure 7:
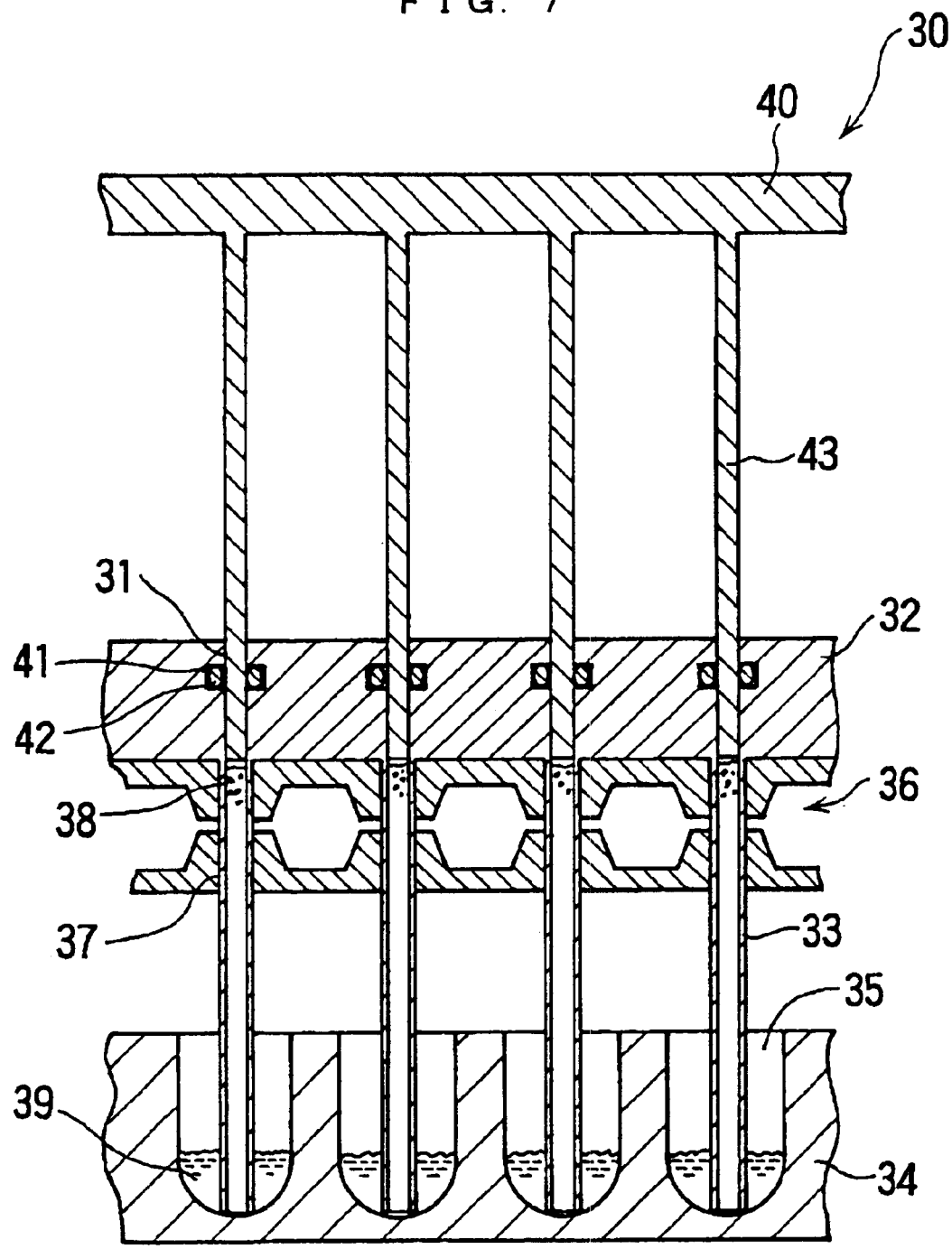
FIG. 7 is a cross-sectional view showing an apparatus for an integrated process according to a third embodiment of the present invention.

Next, an apparatus 30 according to a third embodiment, is described on the basis of FIG. 7.

The apparatus 30 according to the present embodiment is used for processes for minute amounts of liquid. As shown in FIG. 7, the apparatus comprises a plank-like reservoir body 32 mounted with plural pit-like cylinders 31 arranged in a matrix, serving as plural reservoirs.

Under the reservoir body 32, plural nozzles 33 communicating with the cylinders 31 are formed to be integral with the reservoir body 32 and to be projecting downwards from the reservoir body 32. The size and thickness of the nozzles 33 are determined so that the nozzles 33 can be inserted into liquid containing parts 35 provided in a vessel 34 placed under the apparatus, and have a capacity larger than that of the liquid containing parts 35.

In the apparatus 30 according to the present embodiment, the cylinders 31 communicate with the nozzles 33, and the inside diameter of the cylinders 31 is the same to that of the nozzles 33. The inside diameter of the cylinders 31 and the nozzles 33 is for example, the order of a few mm (about 6 mm in this example).

A transfer mechanism (not shown) is mounted on the reservoir body 32 so that the reservoir body 32 can move to and from the vessel 34 vertically and horizontally. A magnetic force device 36 is mounted, under the reservoir body 32 and above the vessel 34. The magnetic force device 36 comprises plural through sections 37 arranged in a matrix corresponding to the location of the nozzles 33, which have wall parts being in contact with or near the outside of the inserted nozzles 33 and capable of being magnetized and demagnetized. The structure of the magnetic force device 36 is the same to that of the one described in the first embodiment, except for the diameter of the through sections and so on. Above the reservoir body 32, a sliding body 40 capable of moving to and from the reservoir body 32 vertically, is mounted. The sliding body 40 comprises plural plungers 43 serving as sliding projections, which project downwardly from the sliding body 40 and can slide through the cylinders 31. The entire length of the plungers 43 is preferably determined to be the same as or longer than the sum of the depth of the cylinders 31 and the length of the nozzles 31.

Further, the sliding body 40 comprises a mechanism (not shown) for moving to and from the reservoir body 32 vertically. Here, in FIG. 7, reference numeral 38 indicates magnetic particles, reference numeral 39 indicates a liquid which is an object for the process. Further, reference numeral 41 indicates an interior circumferential groove, and reference numeral 42 indicates an O-ring fitted into the groove.

This embodiment is suitable for the case where an amount of liquid is comparatively small and the capillary-like nozzles and the cylinders, being the reservoir, have a small capacity. The cylinders 32, the nozzles 33 and the vessel 34 are preferably formed to be transparent so that the inside can be seen therethrough.

FOURTH EMBODIMENT

Figure 8:
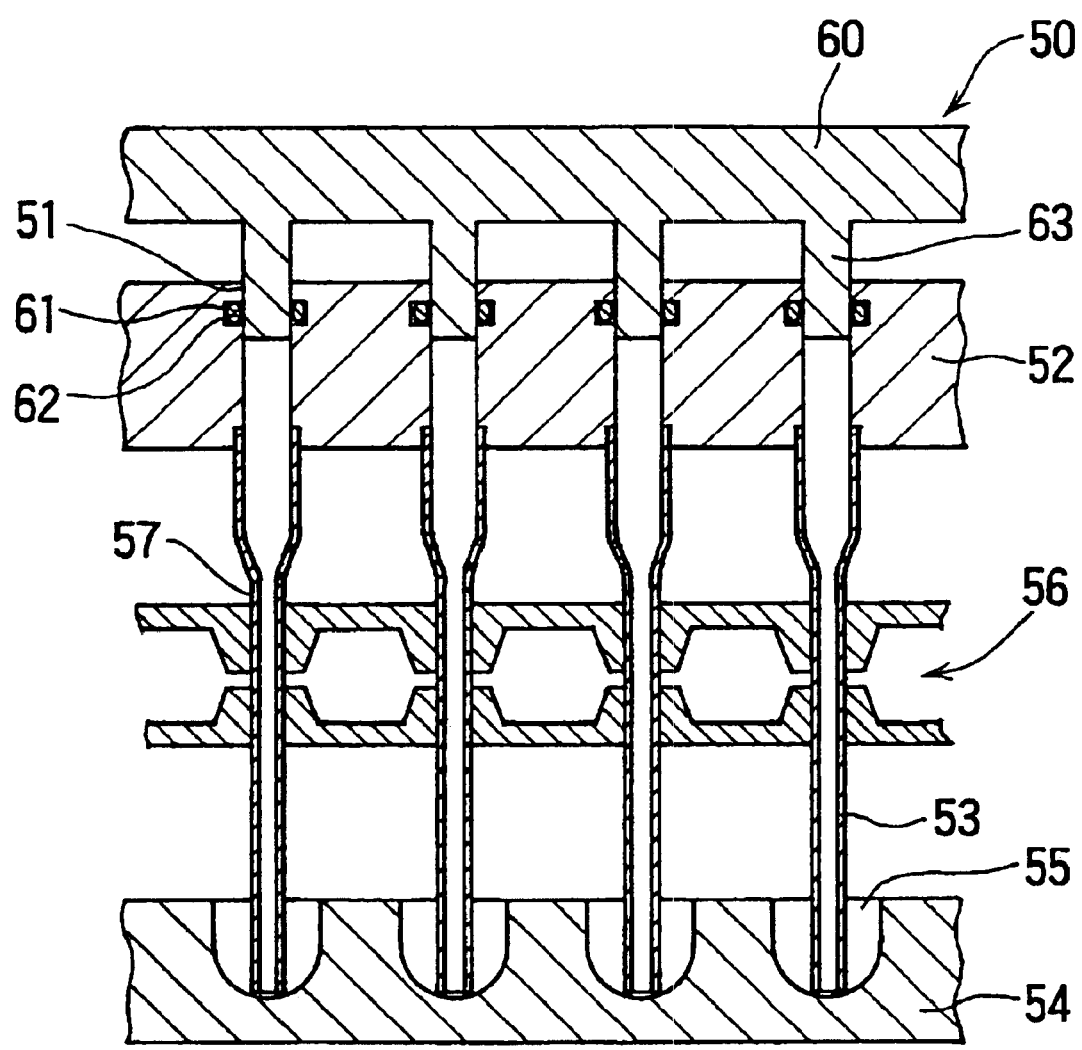
FIG. 8 is a cross-sectional view showing an apparatus for an integrated process according to a fourth embodiment of the present invention.

Next, an apparatus 50 according to a fourth embodiment is described, on the basis of FIG. 8.

The apparatus 50 according to the present embodiment, comprises a plank-like reservoir body 52 where plural pit-like cylinders 51 serving as plural reservoirs, are arranged in a matrix. Plural nozzles 53 communicating with each cylinder 51 are stuck to the lower part of the reservoir body 52, by welding and so on in such a manner that plural nozzles project from the reservoir body 52 downwards.

The length and the thickness of the nozzles 53 are determined so that the nozzles 53 can be inserted into the plural liquid containing parts 55 mounted in the vessel 54 placed under the apparatus 50, and can have a capacity sufficiently large to be that of the liquid containing parts 55. With the apparatus according to the present embodiment, the inner diameter of the cylinders 51 is different from that of the nozzles 53. The apparatus 50 is suitable for processes for liquids of amounts larger than that handled by the apparatus 30 according to the third embodiment.

A mechanism (not shown) is mounted so that the reservoir body 52 and the vessel 54 can move to and from each other vertically or horizontally.

A magnetic force device 56 is mounted below the reservoir body 52 and above the vessel 54. The magnetic force device 56 comprises plural through sections 57 arranged in a matrix and corresponding to the locations of the nozzles 53, with wall parts being in contact with or near the outside of the inserted nozzles 53 and capable of being magnetized and demagnetized. The magnetic force device 56 is the same to that of the first embodiment except for the diameter of the through sections.

Above the reservoir body 52, a sliding body 60 capable of moving to and from the reservoir body 52 vertically, is mounted. The sliding body 60 comprises plural plungers 63 which project downwardly from the sliding body 60 and can slide through the cylinders 51, serving as sliding projections. The entire length of the plungers 63 is preferably determined to be shorter than the depth of the cylinders 51 so that an air layer can be formed between the tips of the plungers 63 and the liquid to be drawn or discharged.

Further, the sliding body 50 comprises a mechanism (not shown) for moving vertically. Here, reference numeral 61 indicates an interior circumferential groove, and reference numeral 62 indicates an O-ring fitted into the groove 61 for preventing leakage of liquid.

FIFTH EMBODIMENT

Figure 9:
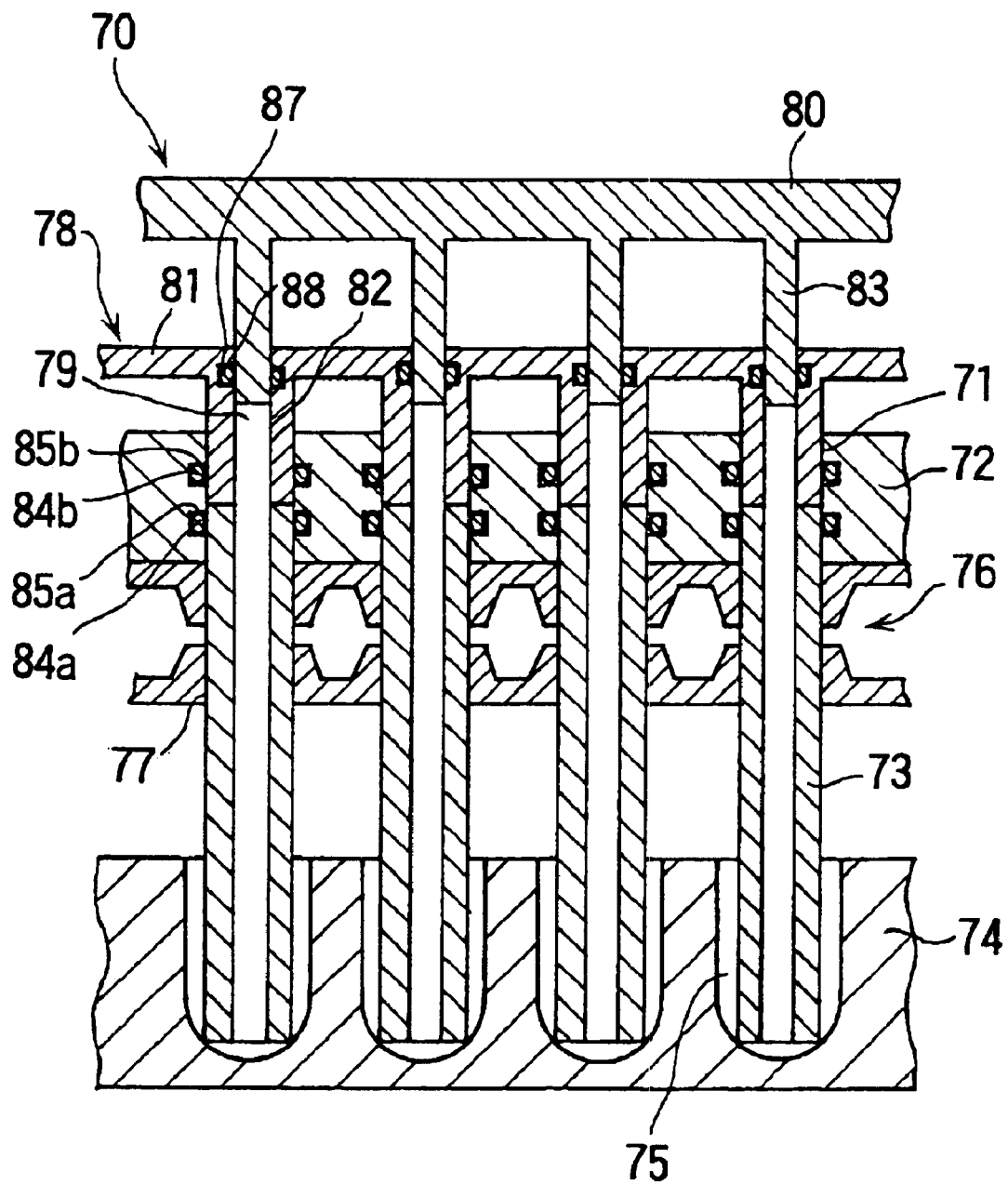
FIG. 9 is a cross-sectional view showing an apparatus for an integrated process according to a fifth embodiment of the present invention.

Next, an apparatus 70 according to, a fifth embodiment is described on the basis of FIG. 9. As shown in FIG. 9, the apparatus 70 according to the present embodiment comprises a plank-like reservoir body 72 arranged with plural pit-like cylinders 71 in a matrix, serving as plural reservoirs.

Under the reservoir body 72, plural nozzles 73 communicating with the cylinders 71 are mounted in such a way that the plural nozzles 73 project downwards from the reservoir body 72. Each nozzle 73 is fitted into the lower part of each cylinder 71 in a manner that the nozzles 73 can be detached.

A pushing body 78 is mounted above the reservoir body 72. The pushing body 78 comprises plural pushing pipes 79 which project downward from a base plate 81 of the pushing body 78, are in contact with the upper parts of the nozzles 73 within the cylinders 71 and are inserted into the cylinders 71 from the upper parts of the cylinders 71 so that the nozzles 73 can be pushed out of the cylinders 71.

Plural thin holes 82 vertically penetrate the base plate 81 and the pushing pipes 79 of the pushing body 78. An interior circumferential groove 87 is provided in each of the thin holes 82, and an O-ring 88 is fitted into the groove 87 so as to prevent leakage of liquid from the thin holes 82.

Further, interior-circumferential grooves 85a, 85b are provided in each cylinder 71, and O-rings 83a, 84b are fitted into the grooves 85a, 85b for securely holding the nozzles 73, respectively. Further, the O-rings 84a serve for preventing leakage of liquid between the nozzles 73 and the cylinders 71, and the O-rings 84b serve for preventing leakage of liquid between the pushing pipes 79 and the cylinders 71. A mechanism (not shown) is mounted so that the reservoir body 72 can move to and from the vessel 74 having the liquid containing parts 75, vertically and horizontally.

A magnetic force, device 76 is mounted under the reservoir body 72 and above the vessel 74. The magnetic force device 76 comprises plural through sections 77 having wall parts being in contact with or near the outside of the inserted nozzles 73 and capable of being magnetized and demagnetized, and arranged in a matrix in a manner corresponding to the location of the nozzles 73 of the reservoir body 72.

A sliding body 80 is mounted above the reservoir body 72, in a manner that the sliding body can move to and from the reservoir body 72, vertically. The sliding body 80 comprises plural plungers 83 that project downwardly from the sliding body 80 and can slide through the thin holes 82 and the nozzles 73.

The entire length of the plungers 83 is preferably determined to be the same as or longer than the sum of the depth of the thin holes 82 and the length of the nozzles 73.

With the present embodiment, liquid can be drawn from or discharged to the liquid containing parts 75 of the vessel 74, by moving the sliding body 80 vertically. Further, the pushing body 78 is mounted on the apparatus 70. Since the pushing pipes 79 are mounted in contact with the nozzles 73 within the cylinders 71, the nozzles 73 can be detached by moving the pushing body 78 downward. Here, a mechanism (not shown) is mounted for moving the sliding body 80 and the pushing body 78 vertically. The pushing body 78 may be moved only downward by hand.

SIXTH EMBODIMENT

Figure 10:
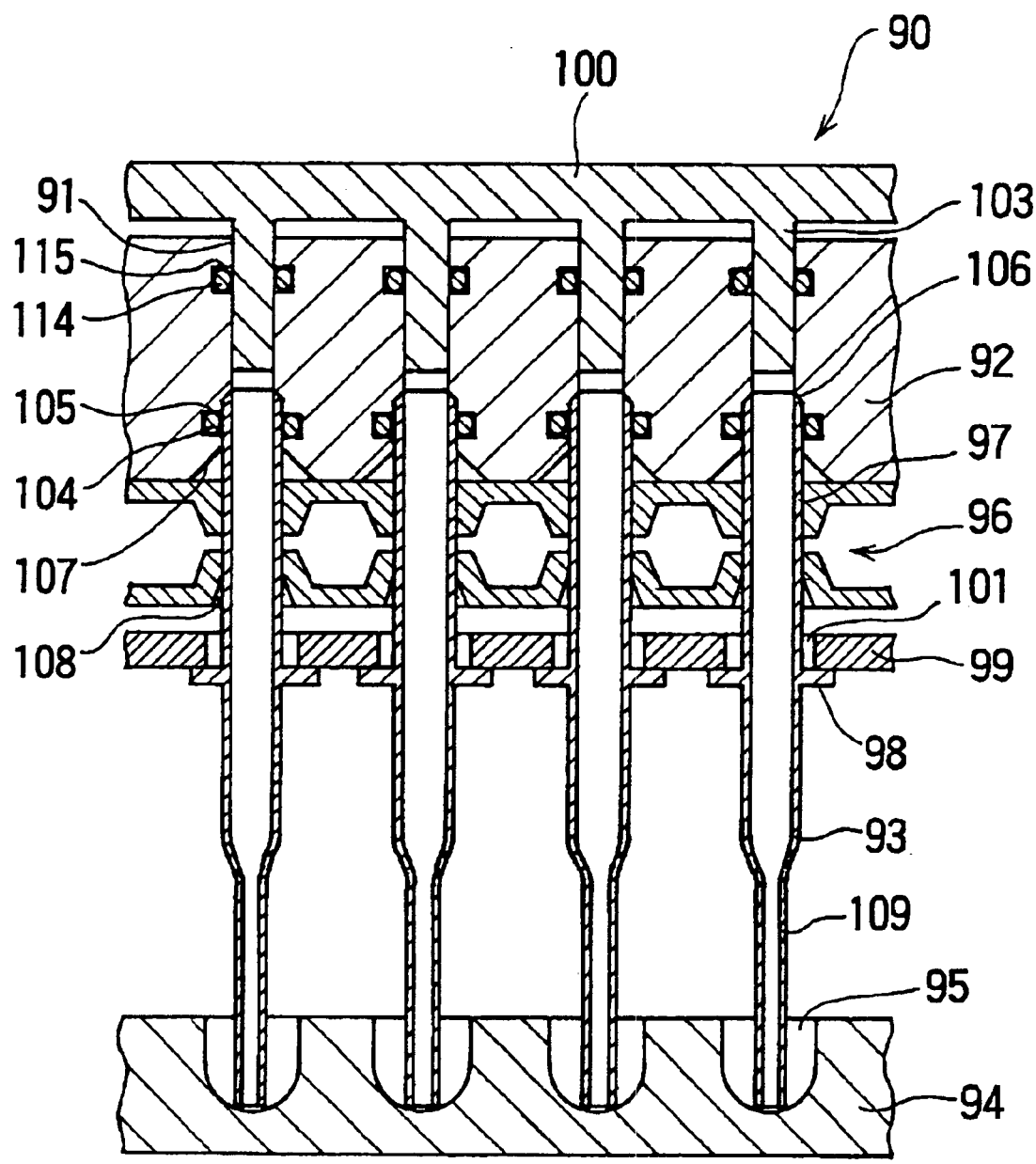
FIG. 10 is a cross-sectional view showing an apparatus for an integrated process according to a sixth embodiment of the present invention.

Next, the apparatus 90 according to a sixth embodiment is described on the basis of FIG. 10. As shown in FIG. 10, the apparatus 90 according to the present embodiment comprises a plank-like reservoir body 92 arranged with plural cylinders 91 in a matrix. Each cylinder 91 of the reservoir body 92 is equipped with a nozzle 93 in a manner that the nozzle 93 is inserted into the cylinder 91 and projects from the reservoir body 92 downward. The length and the diameter of the nozzles 93 are determined so that the lower parts 109 of the nozzles 93 can insert into plural liquid containing parts 95 provided in the vessel 94 placed under the apparatus 90 and have a capacity large enough to store the contents of the liquid containing parts 95. Further a moving mechanism (not shown) is mounted in such a manner that the reservoir body 92 can move to and from the vessel 94 vertically and horizontally. A magnetic force device 96 is mounted under the reservoir body 92 and above the vessel 94. The magnetic force device 96 comprises plural through sections 97 having wall parts being in contact with or near the outside of the inserted nozzles 93 and capable of being magnetized and demagnetized, and arranged in a matrix in a manner corresponding to the location of the nozzles 93. The magnetic force device 96 is the same as the one according to the first embodiment except for the diameter of the through sections and so on.

As exemplified in FIG. 11, a circumferential lip part 98 is mounted around the periphery of the nozzle 93 which is inserted into the through section 97 of the magnetic force device 96, and is exposed below the magnetic force device 96, for detaching the nozzle 93.

Further, as shown in FIG. 10, a stroke-down plate 99 is mounted between the lip parts 98 and the lower surface of the magnetic force device 96. The stroke plate 99 comprises plural small hole parts 101 having a diameter that is larger than that of the nozzles 93 and smaller than that of the lip parts 98, and take insertion of the nozzles 93.

A sliding body 100 is mounted above the reservoir body 24, in a manner that the sliding body 100 can move to and from the reservoir body 92, vertically. Plural plungers 103, serving as plural sliding projections, project downward from the sliding body 100 and can slide inside the nozzles 93. The entire length of the plungers 103 is preferably determined to be the same as or smaller than the length of the nozzles 93.

As shown in FIG. 10, an interior circumferential groove 105 is provided in each of the cylinders 91, and an O-ring 104 is fitted into the groove 105 for securely holding the nozzle 93 and preventing leakage of liquid. Similarly, interior circumferential grooves 115 are provided, and O-rings 114 are fitted into the grooves 115 for preventing leakage of liquid from openings between the plungers 103 and the cylinders 91.

As shown in FIGS. 10 and 11, it is preferable that beveling is executed at an edge of an opening 106 in the upper part of each nozzle 93, so that the nozzles 93 can be easily inserted into the cylinders 91. From the same reason, it is preferable that beveling is executed at an edge of an opening 107 in the lower part of each cylinder 91 and an edge of an opening 108 in the lower part of each through section 97.

Further, a mechanism (not shown) for moving the sliding body 100 vertically is provided. In order to detach the nozzles 93 from the reservoir body 92, the lip parts 98 can be pulled out downward by moving the stroke-down plate 99 downwards and catching the lip parts 98 with the small hole parts 101.

SEVENTH EMBODIMENT

Next, a method of controlling an apparatus according to a seventh embodiment is described on the basis of FIG. 12.

In the present embodiment, four bases constituting DNA, namely A (adenine), G(guannine), T(thymine), C(cytosine) or four bases constituting RNA, namely A (adenine), G(guannine), R(uracil), C(cytosine) are used as elements of substances. The integrated process for generating combined substances having structures of base sequences of seven bases which are arbitrarily combined with each other are shown on the basis of FIG. 12. Necessary equipment used for this process is for example, the apparatus arranged with nozzles in a matrix of 64 rows×64 columns, a multi-nozzle device with 64 multi nozzles 131, 132, 133 134, and seven kinds of vessels 141–147 having liquid containing parts arranged in a matrix of 64 rows×64 columns.

As shown in FIG. 12, at step S1, liquids incorporating each base are dispensed into each liquid containing part of each vessel (reagent plate) 141–147 by using the multi nozzle apparatus 131, 132, 133, 134, in a row-like state or a column-like state of having predetermined widths shown in the figure (one, four, sixteen). Here, magnetic particles serving as carriers, may be dispensed and disposed beforehand, before dispensing the liquids incorporating the base.

At step S2, the nozzles of the apparatus for an integrated process are positioned on the vessels (not shown) accommodating the suspension incorporating the magnetic particles in such a manner that each nozzle faces each liquid containing part, by transferring the apparatus, the devices or the stage on which the vessel is placed. Then, the magnetic force device is driven so that the magnetic field is applied to the nozzles all together, while drawing the specimens. Therefore, the magnetic particles adhere to and are held on the inner walls of the nozzles. Thereafter, the residual liquid after the magnetic particles have been captured and separated, is discharged to the vessels all together. While the apparatus holds the magnetic particles, the apparatus or the stage is transferred to a place over the vessel 141 whose liquid containing parts accommodate a liquid incorporating A-base and is positioned in such a manner that each nozzle faces each liquid containing part. After the nozzles of the apparatus are inserted into the liquid containing parts, the magnetic force device demagnetizes the wall parts all together.

On this occasion, generation of residual magnetization may be prevented by reversing the direction of the magnetization with a strength or driving time according to the strength or driving time immediately before demagnetization. Thereafter, the magnetic particles are resuspended in the liquid by drawing and discharging a suspension incorporating A base accommodated in the vessel 141 all together with the drawing/discharging devices of the apparatus. The apparatus mixes and agitates both suspensions by repeating drawing and discharging. A substance for combining A-base with the magnetic particles is coated on the surface of the magnetic particles beforehand.

The A-base combines with the surface of the magnetic particles, by agitating and mixing. In order to combine the surface of the magnetic particle 38 with only one A-base, the speed, time, number of times of drawing and discharging or predetermined reagents may be controlled.

Thereafter, the apparatus drives the magnetic force device to apply the magnetic field to the nozzles, all together again so that the magnetic particles combined with A-base can adhere to the inner walls of the nozzles and be captured and separated, while the drawing/discharging device draws the entire amount of the suspension from the vessel 141. Then, the accumulation of residual magnetization may be prevented by canceling the magnetization by reversing the direction of magnetization with respect to the immediately previous direction thereof The residual liquid after the magnetic particles have been separated, is discharged from the nozzles of the apparatus in a state with the magnetic field applied to the nozzles.

At step S3, the apparatus or the stage on which the vessel is placed is transferred horizontally to the vessel 142 in a state with the magnetic particles adhering to the inner walls of the nozzles. Then each nozzle of the apparatus for an integrated process is positioned so that each nozzle faces each liquid containing part of the vessel 142. As show in the figure, each base, A, G, T, C is dispensed in each group of 16 rows of liquid containing parts beforehand. The nozzles are inserted into the liquid containing parts by lowering the nozzles of the apparatus downward all together, and the magnetic force device is demagnetized all together.

On this occasion, the demagnetization may be executed after reversing the direction of magnetization, in a manner to cancel the residual magnetization. Thereafter, the magnetic particles are resuspended in the liquid by drawing and discharging each suspension incorporating each A-, B-, C-, D-base respectively, all together. Each base is combined with each A-base having already combined with the magnetic particles. Consequently, as shown in step S3 in FIG. 12, each base sequence such as ●A-A, ●A-G, ●A-T, ●A-C is obtained.

Thereafter, the apparatus drives the magnetic force device to apply the magnetic field to the nozzles, to make the magnetic particles adhere to the inner walls of the nozzles and capture and separate the magnetic particles, while drawing the whole suspension from the vessel 142. On this occasion, the residual magnetization maybe prevented by reversing the direction of the magnetization with respect to that of the magnetization at the previous step S2.

The residual liquid after the magnetic particles are separated, is discharged from the nozzles of the apparatus while the magnetic field is applied to the nozzles.

The following processes at step S4 and step S5 are the same as the process at step S3, except that the arrangement of the base dispensed beforehand is different from that of step S3 in vessels 143, 144 of FIG. 12. On this occasion, the direction of magnetization may be reversed with respect to that of the immediately prior magnetization, for preventing residual magnetization. Thus, at step S4, base sequences such as ●A-A-A and ●A-A-G are obtained as shown in step S4 of FIG. 12. At step S5, base sequences such as ●A-A-A-A and ●A-A-A-G are obtained, as shown in step S5 in FIG. 12.

At step S6, in a state with the magnetic particles adhering to the inner wall of the nozzles, the apparatus or the stage on which the vessel is placed is transferred horizontally and rotated through 90° with a vertical axis (transposing movement) so that the nozzles of the apparatus are positioned over the vessel 155. Consequently, as shown in step S6 in FIG. 12, dispensing and mixing are executed in a transposed arrangement of elements of substances with respect to that at steps S3–S5.

The following process is the same to that of step S3. As a result, as shown in step S6 in FIG. 12, such base sequences as ●A-A-A-A-A can be obtained in the magnetic particles. Similarly, as shown in step S8 in FIG. 12, such base sequences as ●A-A-A-A-A-A can be obtained by going through the processes at steps S7 and S8.

By the above processes at steps S1–S8, $4^6$=4086 kinds of base sequences of seven bases can be obtained. When these processes at steps S1–S8 are executed in the vessel 141, for G, T, C, instead of A-base, $4^7$=16384 kinds of base sequences of seven bases can be obtained in total.

Though only the case of DNA is mentioned, in the above embodiments, RNA, integrated generation of combined substances obtained by the arbitrary combination of elements of substances such as three, five, or ten kinds of amino acids and so on is possible. Further, on the way to the reaction plates, various operations such as cleaning or activation for reaction can be arbitrarily combined. Further, the generation of the above combined substances is executed by using the magnetic particles serving as a carrier, and the apparatus. However, the method of generation is not limited to this case. Instead of using the apparatus, the generation can be executed by using a vessel or column cluster having a function of capturing the magnetic particles. In this case, such a magnetic force device as can apply and remove the magnetic force in a state that the neighborhood of each liquid containing part in the vessel or column remains stationary, can be used instead of keeping the neighborhood of the nozzles stationary.

Furthermore, instead of the magnetic particles, non-magnetic particles such as high polymer particles, and a vessel or column cluster having a function of capturing the non-magnetic particles may be used.

Though in the above cases the nozzles and liquid containing parts, and the sliding projections etc. are arranged in a matrix of predetermined size, the invention is not limited to these cases. For example, further larger sizes such as 384 items (16 rows×24 columns) may be arranged in a matrix, or these may be arranged in such a close state that each neighboring row or neighboring column is alternately shifted one to the other, or these may be arranged cartridge-like in a row or a column or may be arranged, circularly, annular ring-like, radially, or polygon-like.

The shape of the reservoir body or vessel is not limited to quadrilateral but may be square or circular. When the reservoir body and the nozzles are made of a transparent body or a translucent body, the inside can be seen therethrough, conveniently. The shape of the nozzle or cylinder part is not limited to being cylindrical, but may be a square pillar or cone shape etc.

Here, the apparatus according to each embodiment comprises a controller (not shown). The controller comprises an input means such as a keyboard, a mouse, a CD driver, a floppy disc driver, an IC card of the protocol control method, a touch panel, or a communicating device, a data storing unit for storing programs or data such as a memory, a CD, or a floppy disc, a CPU for executing various instructions on the basis of instructions, programs or data, a display unit for displaying various contents, an outputting device for outputting results of processes, results of measuring, results of experiments, such as a printer, a graphic device, a communicating device, a CD, a floppy disc, and a driving controller for controlling the driving of various mechanisms on the basis of CPU instructions. In short, the apparatus according to the present, invention is equipped with various devices necessary for control. Another example of the magnetic force device is shown in FIG. 13.

EIGHTH EMBODIMENT

As shown in FIG. 13(a), a magnetic force device 165 according to an eighth embodiment comprises an upper plate 185a and a lower plate 185b which are mounted oppositely at a predetermined interval, made of a non-magnetic material such as resin, and plural pillars 175a sandwiched between the two plates 185a, 185b and connecting between the plates, made of a magnetic or non-magnetic material. At each pillar 175a, a through section 175 capable of taking insertion of a nozzle 13 is provided in a manner penetrating the plates 185a, 185b vertically. The outside of each pillar part 175a is provided with a coil which is wound by a wire 195 in a manner that the through section 175 is enclosed. The wire 195 constitutes the electromagnet capable of generating and extinguishing a magnetic field by connecting with a switch and a power source (not shown). By the present structure, since a magnetic field can be generated at point blank range of the nozzle 13, a strong magnetic field can be generated. Further, since the coil is not mounted on the nozzle, the nozzle per se can be disposed.

The wire 195 may be separate in each through section 175, or may be commonly used with plural through sections or with all through sections.

Here, each pillar part 175a may be mounted separate from the upper plate 185a and the lower plate 185b, or may be mounted integral with either the upper plate 185a or the lower plate 185b. In these cases, after the coils are fitted, the coils are fixed by securing with the lower plate 185b or the upper plate 185a.

NINTH EMBODIMENT

A magnetic force device 166 according to a ninth embodiment, shown in FIG. 13(b) comprises a plank plate made of a magnetic body, and the through section is through holes 176 provided in the plank plate and capable of taking insertion of the nozzles. In this case, the magnetic field is applied by the magnetic source 196, not vertically but horizontally. FIG. 13(c) is a cross-sectional view of the magnetic force device.

Thus, the structure of the magnetic force device can be simplified. In this case, as shown in FIG. 13(d), by using a magnetic force device with piled up thin plates of magnetic materials (normal direction of the plate may be vertical or horizontal), a uniform magnetic field can be applied without leakage of the magnetic field.

TENTH EMBODIMENT

As shown in FIG. 13(e), a magnetic force device 167 according to a tenth embodiment applies a magnetic field from left to right in the drawings, being different from the aforementioned first embodiment. A gap 177a is formed in a manner penetrating each through hole 177 perpendicularly in the drawings. The wall part of each through hole 177 is thus divided into left and right and the gap 177a has the shortest distance within the magnetic force device and each divided wall part has opposite polarities.

ELEVENTH EMBODIMENT

As shown in FIG. 13(f), a magnetic force device 168 according to an eleventh embodiment applies a magnetic field from left to right in the drawings. A gap 178a is formed in a manner that the wall part of each through hole 178 is divided perpendicularly into right and left, and has the shortest interval within the magnetic force device and each wall part has opposite polarities. Magnetic sources 198 are mounted on both sides.

Thus, strong magnetic fields can be applied to the nozzle in each through section with a simplified structure. Here, in FIG. 13(e) and FIG. 13(f), the division into up and down and the division into right and left may be combined in a way that the magnetic force is also applied perpendicularly in the drawings.

TWELFTH EMBODIMENT

In FIG. 13(g), a magnetic force device 169 according to a twelfth embodiment is shown. The magnetic force device 169 comprises plural magnetic segments (for example, corresponding to rows of nozzles selected from the plural nozzles arranged in a plane-like state) which are divided so that each segment has a size large enough to maintain the necessary strength of the magnetic force therein.

THIRTEENTH EMBODIMENT

Figure 14:
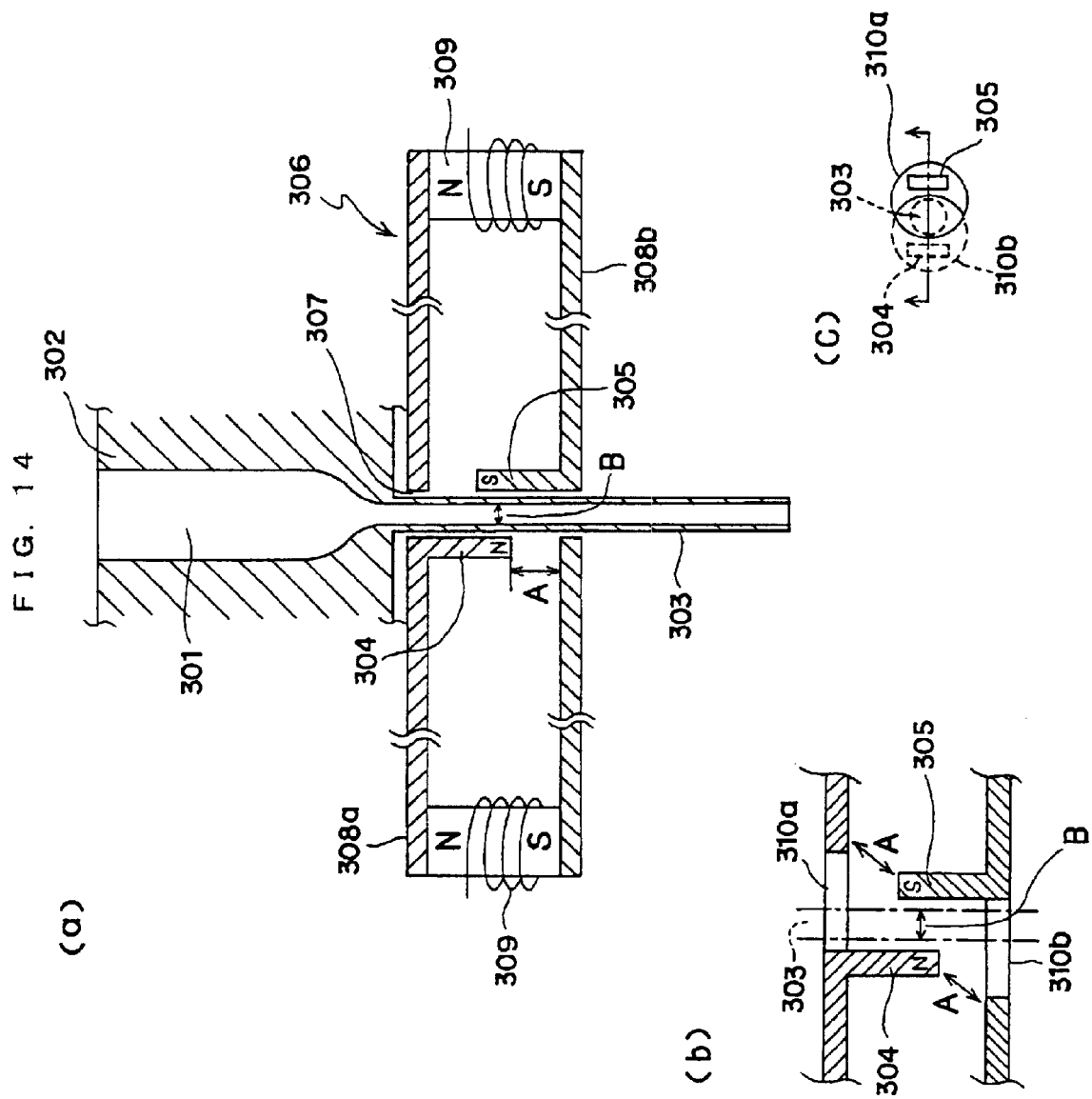
FIG. 14 is a view showing a magnetic force device according to a thirteenth embodiment of the present invention.

A magnetic force device 306 etc. according to a thirteenth embodiment is shown in FIG. 14(a).

The magnetic force device 306 comprises electromagnets (or permanent magnets) 309 serving as a magnetic source, two sheets of magnetic plates 308a, 308b connecting with the electromagnets, facing up and down at a predetermined interval, and capable of magnetization and demagnetization and made of magnetic material, and plural through sections 307 penetrating the two sheets of the magnetic plates 308a, 308b vertically and capable of taking insertion of the nozzles 303.

Further, each through section 307 comprises a pair of projections 304, 305 made of magnetic material. The pair of projections 304, 305 project in opposite directions to one another, towards the opposite surface, and each tip of the projections 304, 305 is apart from each opposite surface at a first interval "A", and the tips of the projections 304, 305 are apart from one another at a second interval "B", and each projection has an opposite polarity to the other. Reference numeral 302 indicates the reservoir body, and reference numeral 301 indicates the reservoirs. The pair of projections 304, 305 correspond to the divided parts of the nozzle outer member.

With the magnetic force device 306 according to the present embodiment, the second interval "B" is formed to be shorter than the first interval "A". Consequently, lines of magnetic force or flux lines are formed between the tips of the projections 304, 305 more densely than those formed between the tips of the projections and the magnetic plates 308a, 308b. Consequently, a strong magnetic field can be applied to the nozzles 303 horizontally.

FIGS. 14(b)(c) shows the through holes 310a, 310b whose openings are enlarged by removing opposite areas near each tip of projections 304, 305 in each magnetic plate 308a, 308b. In this case, the first interval "A" between each projection 304, 305 and the opposite area is lengthened to be longer than the second interval "B", and more lines of magnetic force or more dense flux lines can pass through the second interval "B". In this example, the size of the opening of each through hole 310a, 310b may be formed to be equal to the other, and the position of the center of each hole may be shifted sufficiently so that the tip of the nozzle can pass through the two holes.

FOURTEENTH EMBODIMENT

Next, a magnetic force device 316 according to a fourteenth embodiment, is described on the basis of FIGS. 15(a), (b), (c). As shown in FIG. 15(a), the magnetic force device 316 according to the present embodiment comprises, a magnetic source 317, two sheets of magnetic plates 318a, 318b mounted in face-to-face relationship at a predetermined interval and made of magnetic material capable of being magnetized and demagnetized, and plural through sections 320 penetrating the two sheets of the magnetic plates 318a, 318b vertically, and capable of taking insertion of the nozzles and arranged in a matrix.

A magnetic source 317 is mounted out of the space sandwiched by the magnetic plates 318a, 318b. The magnetic source 317 comprises magnetic elements 317a, 317b, 317d, and a coil 317c. The magnetic elements 317a, 317b, 317d comprise a first part 317a, a second part 317b, and an iron core 317d being mounted with a coil 317c, which are formed separate to each other. An end of the first part 317a connects with the magnetic plate 318a, an end of the second part 317b connects with the magnetic plate 318b, and the other end of the first part 317a and the other end of the second part 317b connect with each end of the iron core 317d mounted with the coil 317c and are fixed by screws or the like.

The magnetic elements 317a, 317b, 317d and the both edges of the magnetic plates 318a, 318b that are not faced each other at the edges, are formed to be horseshoe-like as a whole. Reference numeral 319 indicates a spacer made of a non-magnetic body and mounted between the magnetic plate 318a and the magnetic plate 318b.

FIG. 15(b) is a side view of the magnetic force device 316 shown in FIG. 15(a). In each through section 320 of the magnetic force device 316, as shown in FIG. 15(b), a pair of projections 322a, 322b are mounted, which project toward the facing surface of the magnetic plates 318a, 318b respectively, and are made of magnetic material, and whose tips are apart from each other.

As shown sectionally with the enlarged upper part of FIG. 15(c), at each position of the pair of the projections, a hole penetrates the magnetic plates 318a, 318b and the pair of projections 322a, 322b vertically, so that the nozzle can be inserted therein.

The lower part of FIG. 15(c) is an enlarged sectional view of a pair of projections according to an other example. The pair of the projections 323a, 323b project from the magnetic plate of the opening edge of the through section toward the facing surface in the opposite direction to each other. The tips of the projections are apart from the facing surface at a first interval A respectively, and are apart from each other separated from the nozzle 321 at a second interval "B" shorter than the first interval, in such a manner that they have opposite polarities by magnetization, respectively.

With the present embodiment, since the magnetic source 317 is mounted outside of the space sandwiched by the magnetic plates 318a, 318b, the turn number of wound wire of the coil 317 is not restricted by the interval between the two magnetic plates 318a, 318b. With the embodiment, the amount of wire wound on the coil 317c can be increased, according to the width of the magnetic plates 318a, 318b and the length of the magnetic elements 317a, 317b. Further, plural coils may be mounted in parallel, in the magnetic force device. Consequently, a strong magnetic field can be provided, without extending the interval between the two magnetic plates.

Though in the present embodiment, the first part 317a, the second part 317b and the iron core 317d are described as being separate to each other, the magnetic elements 317a, 317b and 317d may be formed to be in one piece, or further may be formed to be in one piece together with the magnetic plates 318a, 318b. In the case where they are formed to be separate to each other, production can be facilitated because they can be divided into a simple form, in comparison to the case where they are formed to be in one piece. Further, the coil may be formed by winding wire around the overlapped ends of the first part and the second part.

Figure 15:
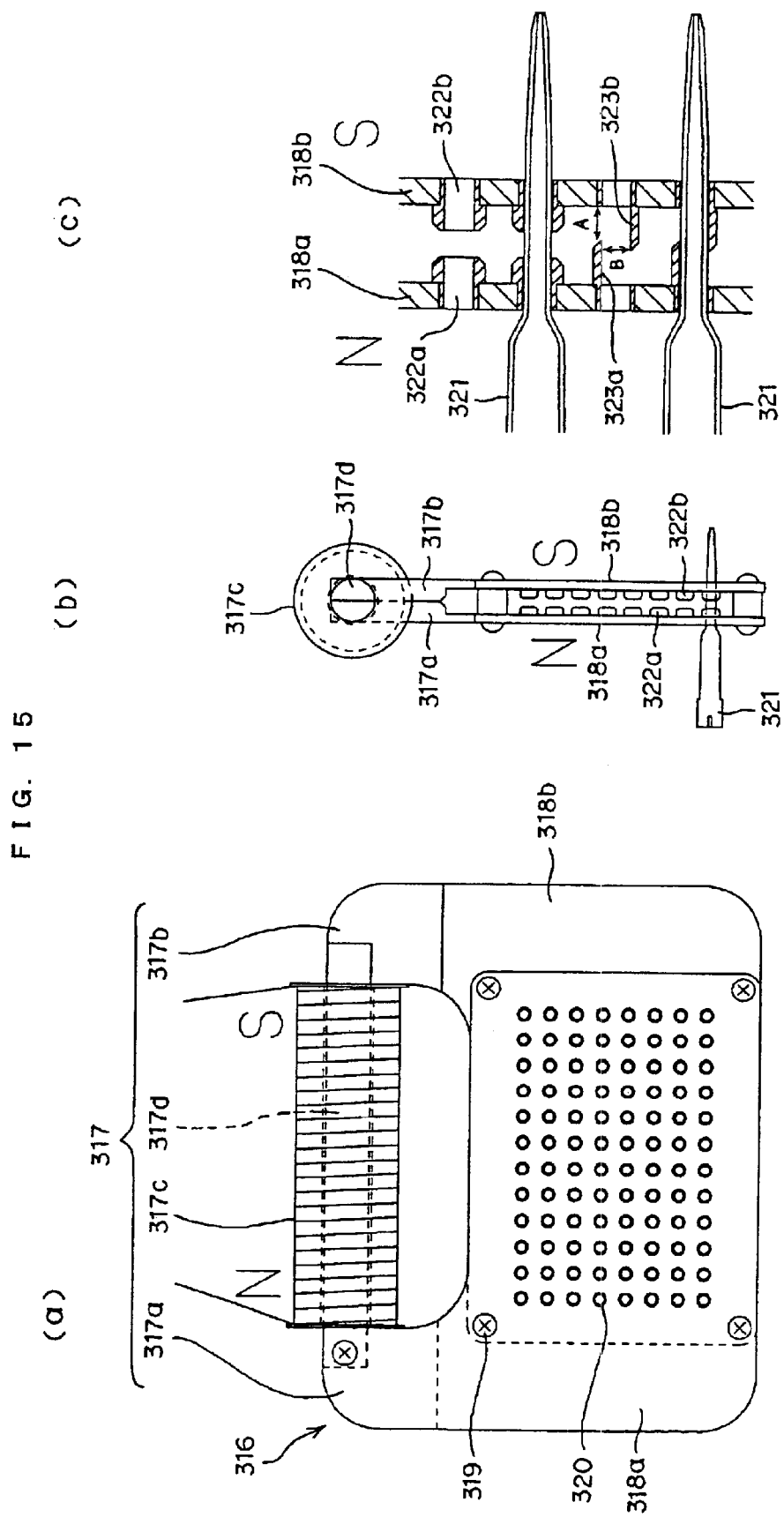
FIG. 15 is a view showing a magnetic force device according to a fourteenth embodiment of the present invention.

Though the magnetic force devices according to the present embodiment, shown in FIGS. 15(a), (b), (c) are described for the case where only one magnetic source is mounted, as shown in FIG. 16, two magnetic sources 325, 327 may be mounted outside of the space sandwiched by the, magnetic plates 328a, 328b and both sides of the magnetic plates 328a, 328b, in such a manner that the axes of the magnetic sources 328a, 328b are facing each other and in a horizontal plane with the plane parallel with the magnetic plates 328a, 328b. As described in FIG. 15, each magnetic source 325, 327 comprises coils 325c, 327c, and magnetic elements 325a, 325b, 325d, and 327a, 327b, 327d, respectively. The magnetic elements comprise first parts 325a, 327a, second parts 325b, 327b, and iron cores 325d 327d wound by the coils 325c, 325c which are formed to be separate to each other. Ends of the first parts 325a, 327a connect to the magnetic plate 328a with the magnetic plate 328a diagonally therebetween, and other ends of the second parts 325b, 327b connect to the magnetic plate 328b with the magnetic plate 328b diagonally therebetween.

The other ends of the first parts 325a, 327a and the other ends of the second parts 325b, 327b connect to each end of the iron cores 325d, 327c wound by the coils 325c, 327c, and are fixed by screws or the like.

Here, the magnetic plates 328a, 328b as well as the magnetic plates 318a, 318b are disposed in plane-parallel face-to-face relationship at a predetermined interval and are made of a magnetic material capable of magnetization and demagnetization. Plural through sections 329 capable of taking insertion of the nozzles, penetrate the two magnetic plates 328a, 328b vertically. Further, the structure of each through section 329 is the same as the one shown in FIG. 15(c). With the present embodiment, a stronger magnetic field can be supplied in comparison to the one having a single magnetic source. Here, though the ,embodiment with two magnetic sources is described, a plurality of magnetic sources, such as three or four magnetic sources used in a like manner also falls within the scope of the present invention.

FIFTEENTH EMBODIMENT

Figure 17:
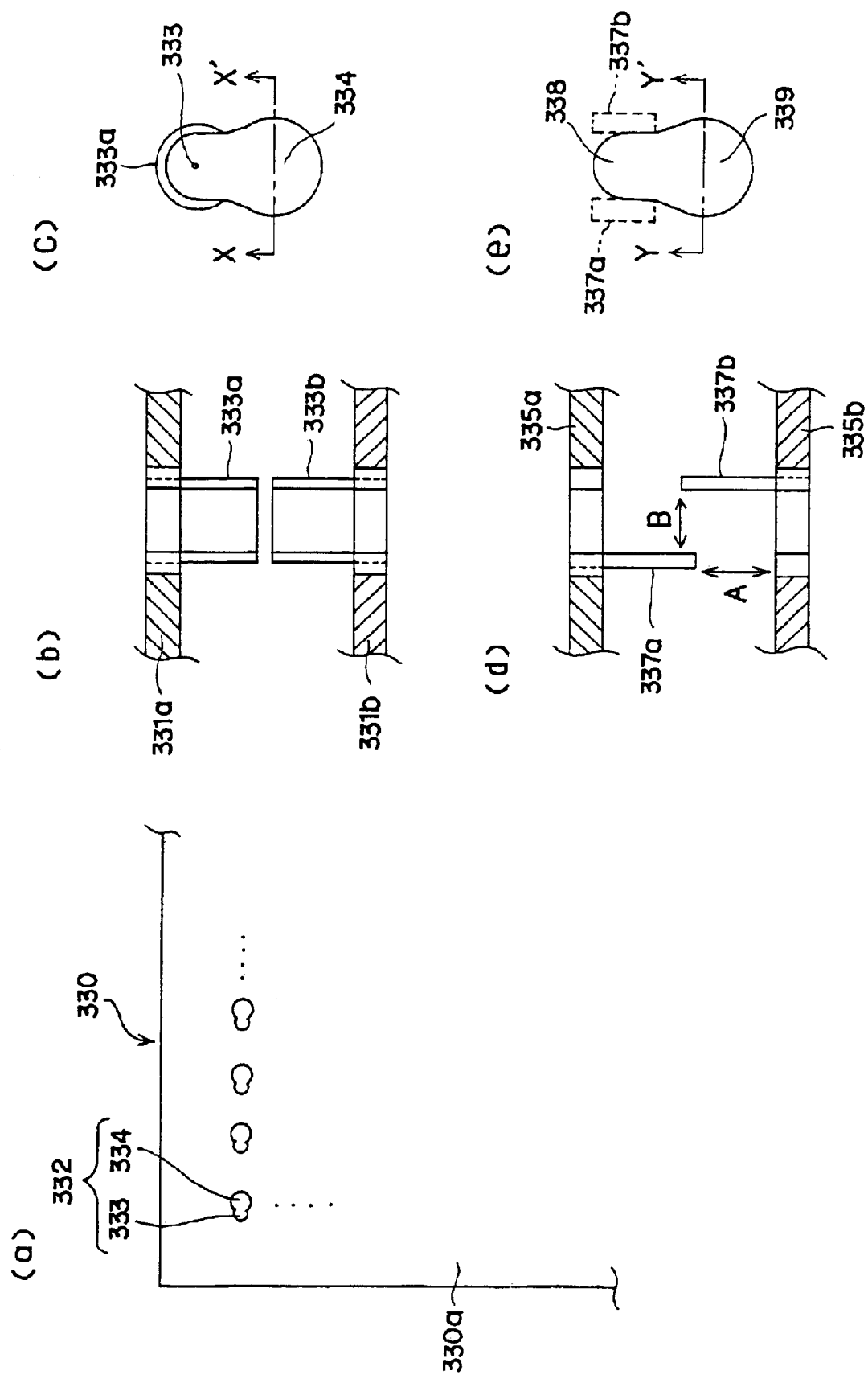
FIG. 17 is a view showing another magnetic force device according to a fifteenth embodiment of the present invention.

A magnetic force device 330 according to a fifteenth embodiment is shown in FIG. 17. The magnetic force device 330 according to the fifteenth embodiment, is used in the case where the nozzles comprise a pipette tip capable of being mounted and dismounted. The magnetic force device 330 according to the fifteenth embodiment, enables the pipette tip to be inserted into or detached from the through section 331 of the magnetic force device 330 without cross contamination.

As shown in FIG. 17(a), the magnetic force device 330 comprises an electromagnet (or a permanent magnet) serving as a magnetic source (not shown), two magnetic plates 331a, 331b magnetically connected to the electromagnet, mounted in face-to-face-relationship at a predetermined interval, in the low and high positions, respectively, and made of a magnetic material capable of magnetization and demagnetization, plural through sections 332 penetrating the two magnetic plates 331a, 331b vertically and capable of taking insertion of the pipette tips serving as the nozzles. The number of through sections 332 is the same as or more than that of the pipette tips of the apparatus. When the connecting relation between the magnetic source (not shown) and each magnetic plate 331a, 331b is such as shown in FIG. 15, the magnetic plate 31a is magnetized for example to have N polarity, and the magnetic plate 331b to have S polarity.

FIG. 17(c) is a plan view of the through section 332. A cross-sectional view taken on line X–X' of FIG. 17(c) is shown in FIG. 17(b). Each through section 332 comprises a separate hole 333 whose nozzle outer member is in contact with or near the periphery of the pipette tip when the pipette tip serving as the nozzle is inserted therein, and an insert-withdraw hole 334 mounted adjacent to the separate hole 333 and capable of horizontal transfer of the pipette tip to and from the separate hole 333 and having an opening larger than that of the separate hole, for inserting and detaching the pipette tip.

The nozzle outer member of the separate hole 333 is a pair of projections 333a, 333b which project toward the facing surface of the magnetic plates 331a, 331b near the opening of the separate hole 333, made of a magnetic material and can take insertion of the pipette tip and are formed to have a somewhat "C" shaped transverse cross-section and a cylindrical configuration, and the tips of which are apart from each other.

The projections 333a, 333b do not enclose the sides of the pipette tip completely, so that an opening capable of passing the pipette tip therethrough is formed for joining with the insert-withdraw hole 334 spatially. In this case, the projections 333a, 333b may be formed so as to be integral with the magnetic plates 331a, 331b, or may be formed so as to be separate from each other and so as to be fitted into holes formed in the magnetic plates 331a, 331b.

The reason for providing the insert-withdraw hole 334 as well as the separate hole 333, is as follows:

Liquid adhering to the lower peripheral part of the pipette tip which comes in contact with the accommodated liquid, will contaminate the magnetic force device 330 by coming in contact with the separate hole 333 or the projections 333a, 333b while withdrawing the tip from the through section 331, or the liquid adhering to the contaminated separate hole 333 etc. may contaminate the newly equipped pipette tip by coming in contact with the pipette tip while inserting the tip into the through hole 331. Consequently, withdrawal or insertion is executed through a hole that has a larger diameter than that of the periphery of the pipette tip in order to prevent such cross contamination.

FIGS. 17(d), (e) shows another example of the through section of the magnetic force device. In this example, the through section 332 comprises a pair of projections 337a, 337b. The pair of projections project toward the facing surfaces from the magnetic plates 336a, 335b at the edge of the opening of the through section 332 in opposite directions respectively, and are made of magnetic material and are spaced apart from one another in a manner so as to have opposite polarities by magnetization. The tips of the pair of projections are apart from the facing surface at a first interval "A", and are apart from one another at a second interval B shorter than the first interval. The magnetic plates 335a, 335b in the parts facing the projections, may be removed in order to extend the interval "A" further.

SIXTEENTH EMBODIMENT

Figure 18:
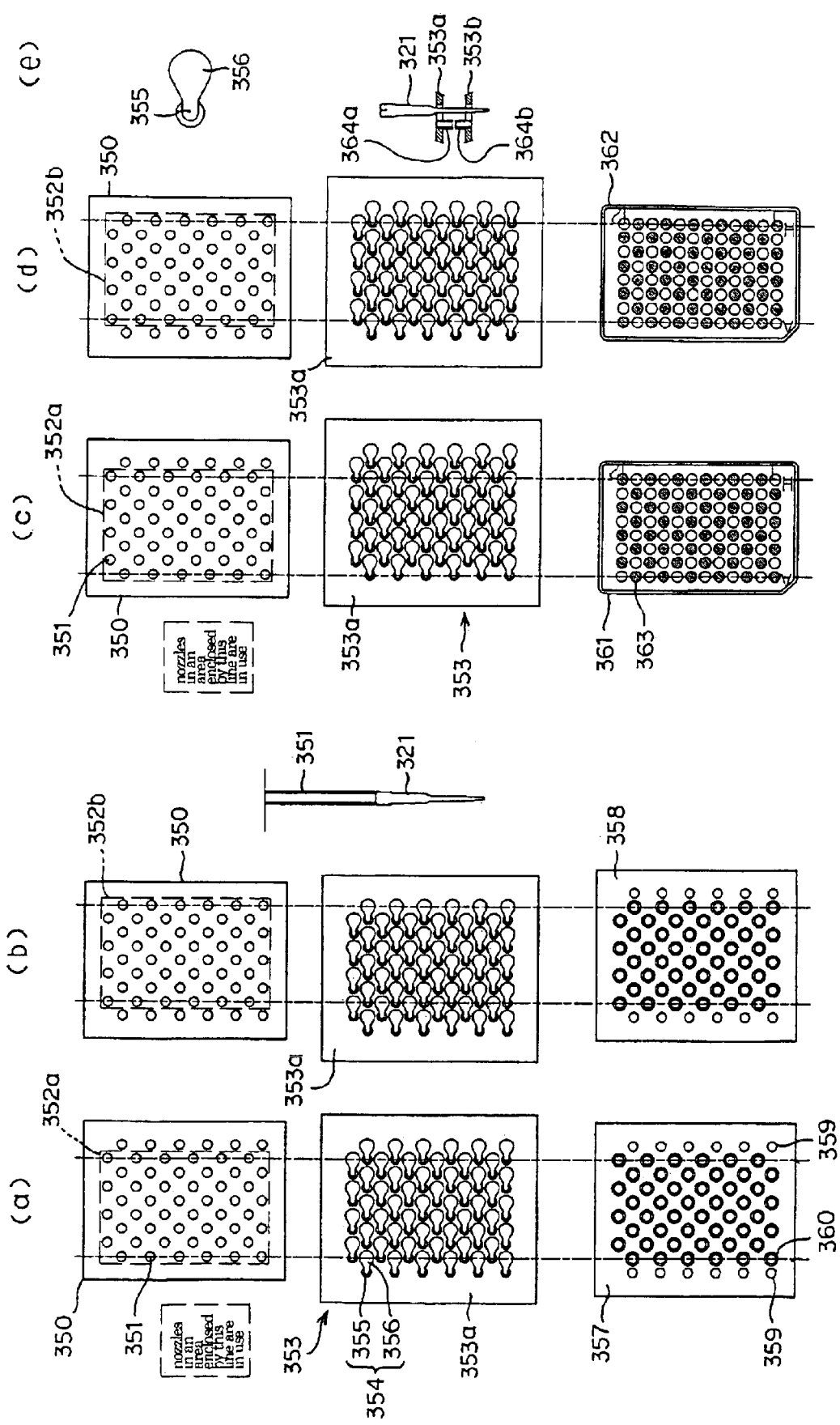
FIG. 18 is a view showing a magnetic force device according to a sixteenth embodiment of the present invention.

Next, a magnetic force device 353 according to a sixteenth embodiment is described on the basis of FIG. 18. In the apparatus according to the present embodiment, plural nozzles are mounted in the reservoir body 350 that constitutes the drawing/discharging device. The nozzles each comprise a fitting part 351 and a pipette tip 321 fitted to the lower part of the fitting part 351 in a way that the pipette tip 321 can be detached. The tip 321 comprises a two-step structure comprising a small diameter section and a larger diameter section. A magnetic force device 353 is mounted under the reservoir body 350. FIGS. 18(a)(b) shows tip racks 357, 358 mounted under the magnetic force device 353 for the fitting and detaching of the pipette tips, and FIGS. 18(c)(d) shows a microplate 361 having 96 wells (liquid containing parts, 8 rows×12 columns) for drawing or discharging.

In regard to the magnetic force device 353, plural through sections 354 capable of taking insertion of each tip 321 are mounted in a way so as to penetrate the two magnetic plates 353a, 353b. The magnetic plates 353a, 353b are magnetically connected to the electromagnet or can be magnetically connected to a permanent magnet, serving as a magnetic source (not shown) respectively. Each magnetic plate 353a, 353b is magnetized in a way so as to have opposite magnetic polarities one to another respectively.

The through sections 354 comprises a separate hole 355 having a diameter capable of taking insertion of only the small diameter section, and an insert-withdraw hole 356 adjacent to the separate hole 355, capable of moving the tip to and from the separate hole 355 horizontally and capable of taking insertion of the larger diameter section of the tip, in a manner forming a pair with the separate hole 355.

As shown in FIG. 18(e), the separate hole 355 penetrates the magnetic plates 353a, 353b and a pair of projections 364a, 364b made of magnetic material. The projections 364a, 364b project toward the facing surface of the magnetic plates 353a, 353b vertically and are formed so as to be capable of taking insertion of the small diameter section of the tip 321. Each wall part of the projections 364a 364b have opposite polarities by magnetization and correspond to the divided parts of the nozzle outer members.

Since the through sections 354 according to the present embodiment can take insertion of the larger diameter section, the through sections 354 are formed so as to be larger than the usual through sections 17, 37, 57, 77, 97 or the through sections 331 according to the fifteenth embodiment, and this results in occupying two portions of the usual through section.

Therefore, all the liquid containing parts in a standard 96 well-microplate 361 which is ordinarily used, cannot be available. As shown by black circles in FIG. 18(c), only 48 liquid containing parts 363, being half of all of the liquid containing parts, can be available. The utilized range 352a of the magnetic force device 353 and the nozzles 351 is shown. The present embodiment enables all the liquid containing parts of the 96 well-microplate 361 to be utilized, by enabling the remaining 48 liquid containing parts, being half of all of the liquid containing parts (refer to the white circles in FIG. 18(c)), to be utilized. This is done by utilizing 54 through sections, and 54 nozzles, in a range of through sections 354 of the magnetic force device 353 and a range 352b of the nozzles.

In order to utilize these 54 sets of nozzles and through sections 354, tip racks 357, 358 are prepared as shown in FIGS. 18(a), (b). The holding places for the tips in the tip racks 357, 358 are different according to the utilized range 352a, 352b of the nozzles. In this case, relief holes 359 capable of preventing the nozzles which do not fall within the utilized range 352a, 353b of the nozzles from collision with the racks 357, 358, are provided on both sides of the 48 holes for holding the pipette tips.

Here, the projections of each through section may have a structure shown not only in FIG. 18(e) but also for example in FIGS. 17(d)(e) (though the diameter of the insert-withdraw hole of this case is larger than the case of FIGS. 17 (d)(e)).

With the present embodiment, since the tips having a small diameter section and a larger diameter section can be completely withdrawn from the through sections of the magnetic force device 353 upward or downward, fitting and detaching the pipette tips can be easily executed.

With the present embodiment, cross contamination generated by contaminating the through sections of the magnetic force device with the liquid adhering to the periphery of the pipette tips can be surely avoided while detaching used pipette tips which have been inserted into the vessels, or fitting new pipette tips.

Further, with the embodiment, since all of the liquid containing parts mounted in the 96 well-microplate 361 can be available, efficiency of usage of the vessel is high.

SEVENTEENTH EMBODIMENT

Figure 19:
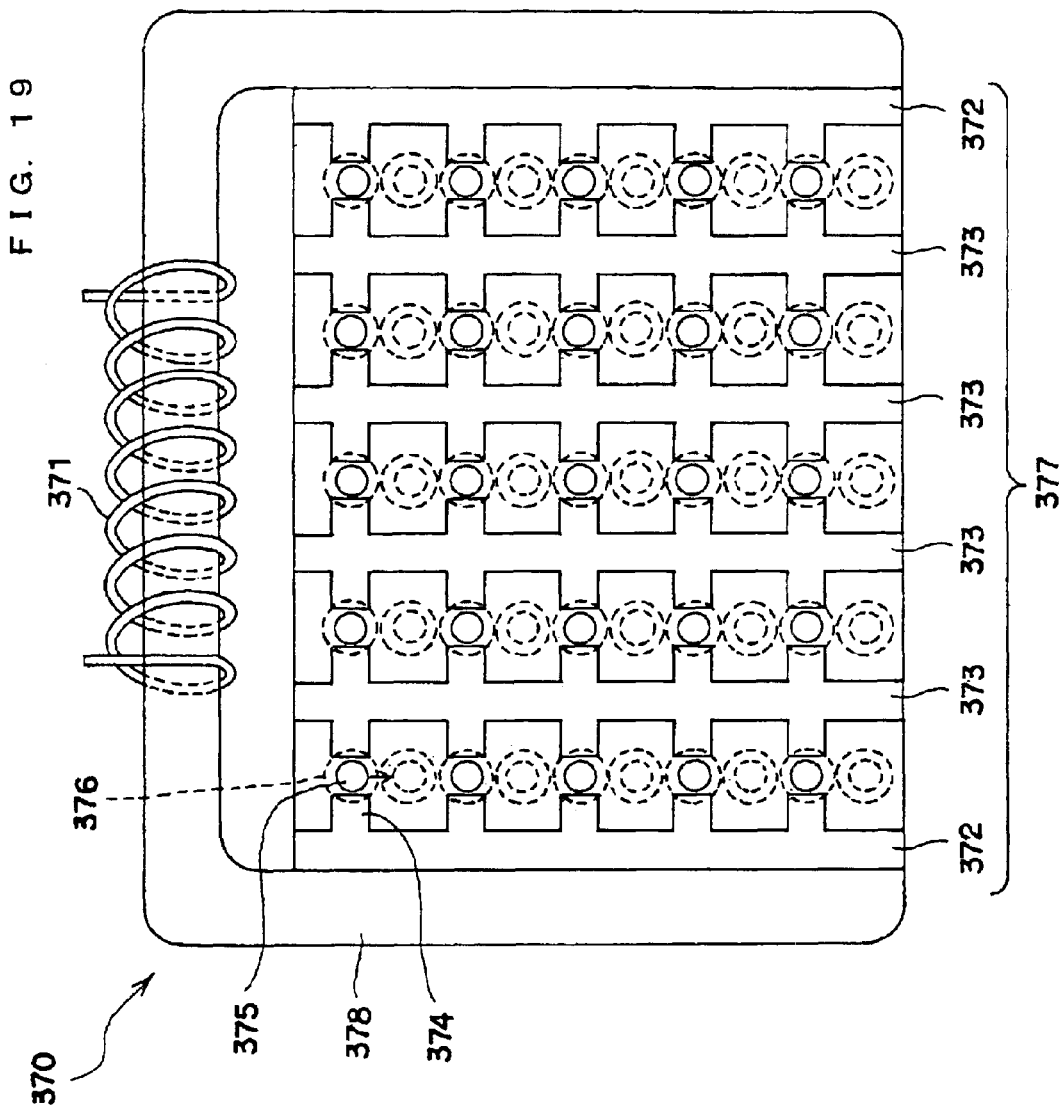
FIG. 19 is a view showing a magnetic force device according to a seventeenth embodiment of the present invention.

Next, a magnetic force device according to a seventeenth embodiment is described on the basis of FIG. 19.

Since the magnetic force device 370 according to the present embodiment is particularly effective when the nozzles thereof have pipette tips comprising a small diameter section 375 and a larger diameter section 376 capable of being mounted and detached, the following descriptions of the present embodiment are devoted to this case.

The magnetic force device 370 comprises a plank member 377 made of magnetic material and magnetically connected, to an electromagnet (or permanent magnet) which comprises a horseshoe-like magnetic element 378 wound by a coil 371 near the center thereof, and serving as a magnetic source. The plank member 377 is divided into plural column-like members 372, 373 separated in such a manner that the intervals between the neighboring column-like members 372, 373 can take the insertion of the larger diameter section 376 of the nozzle. Plural protrusions 374 made of magnetic material project from each column-like member 372, 373 at predetermined intervals facing one an other in a lateral direction of the rows. The facing protrusions themselves are magnetized in a manner so as to have opposite polarities one to another respectively, and are apart from one another with an interval capable of taking insertion of only the small diameter section 375 of each nozzle. Neighboring protrusions 374 mounted in each column-like member 372, 374 are apart from each other so that the larger diameter section 376 can be inserted between the protrusions 374. Tips of the opposite protrusions 374 correspond to the divided wall parts.

With the present embodiment, the tips can be mounted and dismounted in such a manner that the magnetic force device is not contaminated by the liquid adhering to the periphery of the pipette tip and the periphery of the pipette tip is not contaminated by the liquid adhering to the magnetic force device. Consequently, with the present embodiment, cross contamination can be completely avoided in spite of the simple structure.

EIGHTEENTH EMBODIMENT

Figure 20:
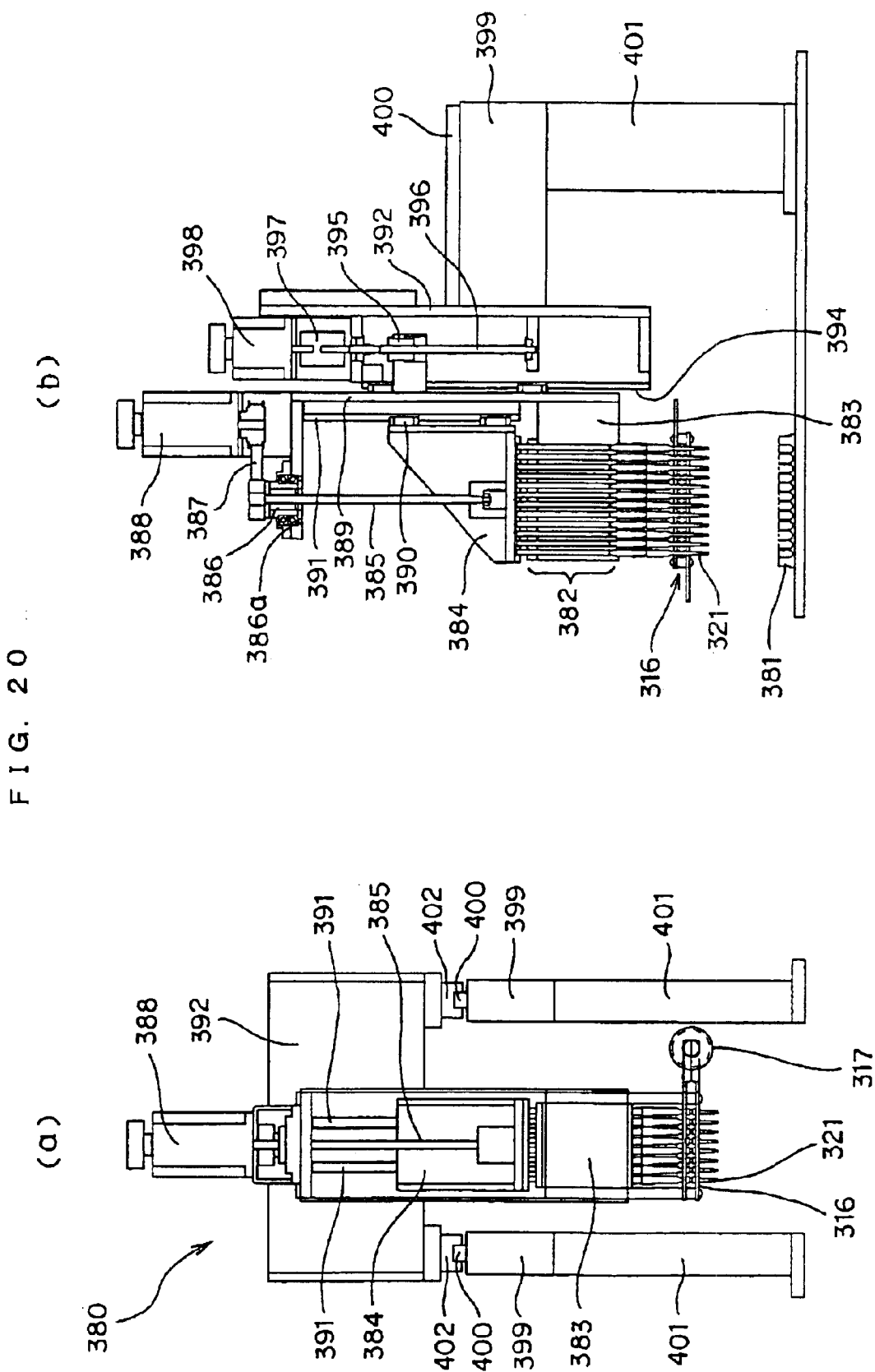
FIG. 20 is a view showing an apparatus for an integrated process according to an eighteenth embodiment of the present invention.
Figure 21:
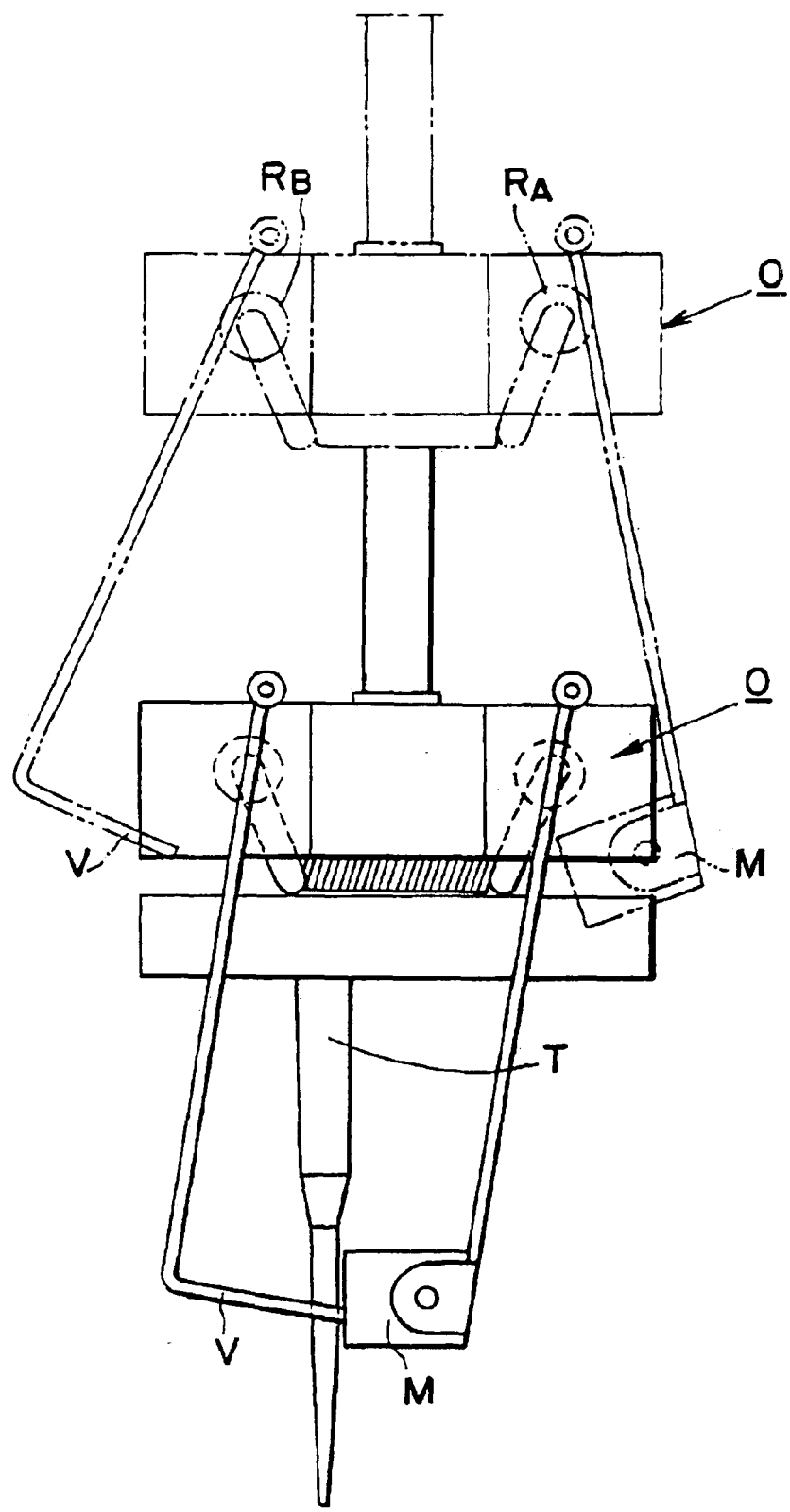
FIG. 21 is a plane view showing an apparatus according to a first prior art.
Figure 22:
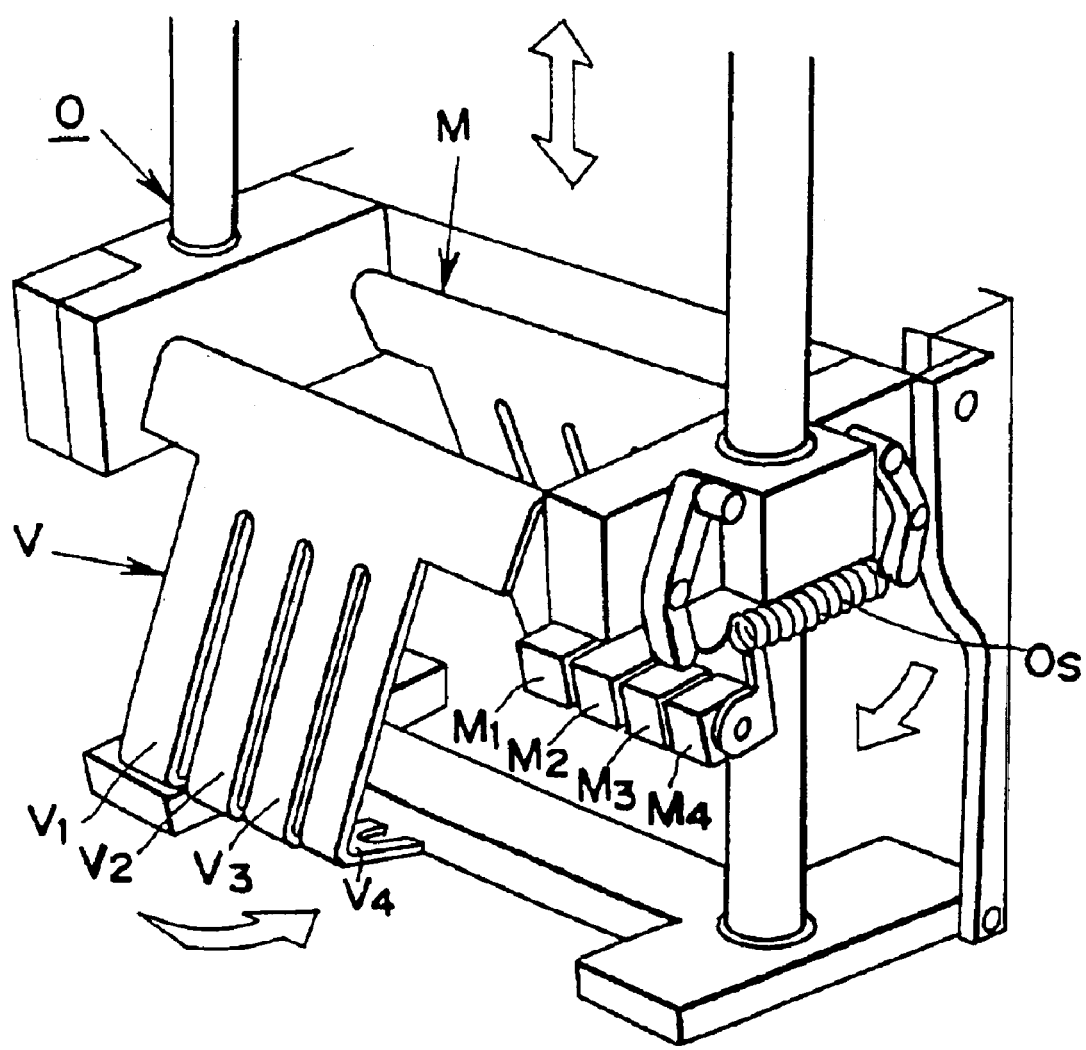
FIG. 22 is a perspective view showing an apparatus according to a second prior art.

An apparatus 380 according to an eighteenth embodiment is described on the basis of FIG. 20. The apparatus utilizes a magnetic force device 316 comprising a magnetic source 317.

The apparatus 380 draws and discharges liquid accommodated in a vessel 381 (a microplate having 8 rows×12 columns in this example) placed under the apparatus 380 and having plural liquid containing parts (wells).

The apparatus 380 comprises a sliding body 384 with projecting plural plungers (96 plungers arranged in a matrix of 8 rows×12 columns, in this example), a reservoir body 383 having plural cylindrical reservoirs 382 (96 reservoirs arranged in a matrix of 8 rows×12 columns, in this example) capable of vertically sliding of the plunger therethrough, plural (96) pipette tips 321 fitted to the lower part of the reservoir 382, and arranged in a matrix (8 rows×12 columns) in a way that the pipette tips 321 can be detached. In the embodiment, the pipette tips 321 are inserted into each of the through sections of the magnetic force device 316, and the lower ends of the pipette tips 321 reach to below the lower magnetic plate by penetrating through the through holes.

The upper part of the sliding body 384 is connected to the lower end of a ball screw 385. The ball screw 385 engages with a nut part 386. The nut part 386 is driven to rotate through a belt 387 by a stepping motor 388. The ball screw 385 moves vertically by rotation of the nut part 386. The reservoir body 383, the magnetic force device 316, and the stepping motor 388 are fixed to a vertical transfer body 389. The sliding body 384 is supported in the vertical transfer body 389 by a translation bearing 390 and a rail 391 laid vertically and guiding the translation bearing 390. Mechanisms such as the reservoir 382, the reservoir body 383, the sliding body 384, the ball screw 385, and the stepping motor 388 constitute the drawing/discharging device.

The vertical transfer body 389 is supported in a back and forth transfer body 392 through a translation bearing 393 and a rail 394 laid vertically and guiding the translation bearing 393 in a way that the vertical transfer body 389 can vertically transfer to and from the back and forth transfer body 392.

The back and forth transfer body 392 comprises a ball screw 396 and a stepping motor 398 driving to rotate the ball screw 396 through a coupler 397. The ball screw 396 engages with a nut part 395 and vertically moves the nut part 395 and the vertical transfer body 389 connected to the nut part 395, by the rotation of the ball screw 396.

Furthermore, the back and forth transfer body 392 can move in back and forth directions, by a translation bearing 402 and a rail 400 laid in the directions, and guiding the translation bearing 402. The back and forth transfer body 392 is supported by a support 399 mounted with a rail 400, and a leg 401.

When the apparatus 380 draws and discharges a liquid from and to the vessel 381 respectively, the apparatus 380 drives the back and forth transfer body 392 to a position over the vessel 381. Next, the lower parts of the pipette tips 321 are inserted into the vessel 381 by vertical transfer of the vertical transfer body 389. Next, a liquid is drawn from or discharged to the vessel 381, by moving the sliding body 384. On this occasion, only a gas, ordinarily air, is drawn to or discharged from the reservoirs 382, and a liquid is drawn to or discharged from the pipette tips 321. Consequently, since the reservoirs 382 do not come in contact with the liquid, the reservoirs 382 are not contaminated by the liquid. The magnetic particles suspended in the liquid adhere to the inner walls of the pipette tips 32 and are separated, or the magnetic particles separated by adhesion to the inner walls of the pipette tips 32 can be resuspended in the liquid by controlling the magnetic force device 316.

The embodiments above have been described in detail to further explain the invention, but in no way preclude other embodiments. Consequently, the embodiments can be altered provided the gist of the invention is retained. For example, the elements of the structure such as the magnetic force device and the nozzle, and the drawing/discharging device of the apparatus can be arbitrarily combined together while executing necessary alterations, and can constitute another apparatus for an integrated process. Further, in the above description, though the method of generating the magnetic field by the magnetic force device is mainly by using an electromagnet, this may also be achieved by a permanent magnet. In this case, the magnetization of the magnetic member is embodied in such a manner that each plate or edge part of the magnetic member comes in contact with or approaches to each magnetic pole of the magnet by rotating the magnet about the axis of the rotation, through 90° and 270° with a vertical axis from an initial position, and demagnetization is embodied in such a manner that each plate or edge part of the magnetic member is taken away from the magnetic pole by for example rotating the magnet toward the initial position. Further, in the embodiments above, it is described that the nozzles and the magnetic force device are formed to be separate. However, the nozzles per se may be included in the magnetic force device, and may be magnetized and demagnetized.

Thus, in the embodiments above, the above objects of the invention are achieved by adopting a method of arranging magnetization in a plane-like state, a method of drawing and discharging all together, and a method of detecting optically all together.

Further, in the embodiments above, though the reservoirs are described as being provided in the block-like reservoir body, the reservoir body may be an aggregation of bundled cylindrical reservoirs.

Further, in the embodiments above, though leakage of liquid is described as being prevented by using O-rings, it may be prevented by using rubber packings provided on the inner wall of the plunger or cylinder, or a combination of rubber packings with O-rings.

Furthermore, in the embodiments above, though it is described that the magnetic force device applies a magnetic force to or removes the magnetic force from each nozzle, this may be applied to or removed from each liquid containing part or each column of the column cluster. The internal diameter of the through section of the magnetic force device is determined on the basis of the diameter of each nozzle, liquid containing part or column. In each embodiment, the magnetic force device may be mounted as the magnetic apparatus on the integrated apparatus, in a way that it can be dismounted therefrom.

Furthermore, it is needless to say that the number and the arrangement of the nozzles, the through sections and the liquid containing parts are interpreted as examples only, and are not interpreted as limitations.

What is claimed is:

1. An apparatus for an integrated process of magnetic particles comprising:

a drawing/discharging device for drawing and discharging a fluid;

plural nozzles arranged in a plane-like state and passing the fluid therethrough while drawing and discharging; and a magnetic force device for applying and removing a magnetic field to and from the nozzles respectively in a manner that the neighborhood of each nozzle exterior remains stationary;

wherein said magnetic force device can apply and remove the magnetic force to and from said nozzles respectively by enabling magnetization and demagnetization in a nozzle outer member brought in contact with or being near the outer surface of said nozzle or at least a part of said nozzle, in a manner that the neighborhood of each nozzle exterior remains stationary;

wherein said magnetic force device comprises a magnetic member made of a magnetic material and provided with a plurality of through sections arranged in a plane-like state and capable of taking insertion of nozzles;

wherein said nozzle outer member is a wall of said through sections; and wherein each through section of said magnetic force device comprises a separate hole in which the nozzle is inserted in a way that the outer surface of the nozzle can come in contact with or approach to the nozzle outer member, and an insert-withdraw hole mounted adjacent to the separate hole and having an opening larger than that of the separate hole so that the nozzle can horizontally move to and from the separate hole and can be withdrawn and inserted at the insert-withdraw hole.

2. An apparatus for an integrated process of magnetic particles according to claim 1, wherein said nozzle comprises a small diameter section and a larger diameter section, said separate hole has an opening that only the small diameter section can be inserted in, and said insert-withdraw hole has an opening that the larger diameter section can be inserted in.

3. An apparatus for an integrated process of magnetic particles according to claim 1, wherein said nozzle outer member of the magnetic force device or a part of said nozzle comprises first and second parts that are spaced from one another in a manner so that the first and second parts have mutually opposite magnetic polarities.

4. An apparatus for an integrated process of magnetic particles according to claim 3, wherein said magnetic force device comprises a magnetic source having an electromagnet or a permanent magnet, the magnetic member comprising two magnetic plates made of magnetic material and connecting with the electromagnet or capable of connecting with the permanent magnet and capable of being magnetized and demagnetized, and mounted in face-to-face relationship in spaced positions, the plural through sections being arranged in a plane-like state, penetrating the two magnetic plates and being capable of taking insertion of the nozzles, and each nozzle outer member comprising a pair of projections mounted in each through section, projecting toward the opposite surface of each magnetic plate and made of magnetic materials, each projection corresponding to one of the first and second parts and the projections of each pair being spaced from one another in such a manner that they have mutually opposite polarities by magnetization.

5. An apparatus for an integrated process of magnetic particles according to claim 4, wherein said through sections comprise through holes penetrating through the magnetic plates and capable of taking insertion therethrough by the nozzles, and each wall part of the mutually separated through holes has opposite polarity respectively.

6. An apparatus for an integrated process of magnetic particles according to claim 4, wherein said magnetic force device comprises one or more of the magnetic sources, each magnetic source comprises a coil and a magnetic element provided with the coil, and one end of said magnetic element is connected with one of the two magnetic plates and the other end thereof is connected with the other of the two magnetic plates.

7. An apparatus for an integrated process of magnetic particles according to claim 6, wherein said magnetic elements are mounted outside of the space which is formed by the magnetic plates.

8. An apparatus for an integrated process of magnetic particles according to claim 7, wherein said magnetic elements comprise a third part and a fourth part which are separately mounted, wherein one end of the third part connects with one of the two magnetic plates, the other end of the fourth part connects with the other magnetic plate, wherein the third part and the fourth part are overlapped and are wound by wire of a coil, or the other end of the third part and one part of the fourth part are connected with each end of a fifth part and wound by wire of the coil and made of magnetic material.

9. An apparatus for an integrated process of magnetic particles according to claim 3, wherein the first and second parts are tapered toward a gap.

10. An apparatus for an integrated process of magnetic particles according to claim 4, wherein said pair of projections each project from the opening edge of the through section of one of the magnetic plates toward the other magnetic plate in a direction of insertion of the nozzle in respective directions opposite to one another, and each tip of the projections is spaced from the opposite surface by a first interval, and the tips of the projections are spaced from one another by a second interval shorter than the first interval, in such a manner that the tips have opposite polarities, respectively.

11. An apparatus for an integrated process of magnetic particles according to claim 1, wherein said magnetic force device comprises plural magnetic sources, and plural segments defined so as to include the area spatially near each magnetic source, respectively.

12. An apparatus for an integrated process of magnetic particles according to claim 1, wherein said magnetic force device comprises a magnetic source having a permanent magnet or an electromagnet, and a member made of magnetic material and magnetically connected to the electromagnet or capable of magnetically connecting to the permanent magnet, wherein the through sections are provided in the member and are capable of taking insertion of the nozzles.

13. An apparatus for an integrated process of magnetic particles according to claim 12, wherein the through holes of the magnetic force device comprise divided wall parts divided in the direction of the insertion of the nozzle in such a manner that divided wall parts are apart from one another and have opposite polarities by magnetization.

14. An apparatus for an integrated process of magnetic particles according to claim 13, wherein the nozzles comprise a larger diameter section and a small diameter section, and the member of the magnetic force device comprises plural column members arranged apart from each other at intervals capable of taking insertion of the larger diameter section of the nozzle, and plural protrusions made of magnetic material that are projected oppositely from each column member, magnetized in a manner that has opposite polarity to each other and arranged apart from each other at intervals capable of taking insertion of the smaller diameter section of the nozzle, and are arranged along the column member at intervals capable of taking insertion of the larger diameter section of the nozzle, wherein opposite pointed ends of the protrusions correspond with the divided wall parts.

15. An apparatus for an integrated process of magnetic particles according to claim 1, wherein said nozzles comprise small diameter pipes communicating with the through sections of the magnetic member and capable of being inserted into a vessel.

16. An apparatus for an integrated process of magnetic particles according to claim 1, wherein said drawing/discharging device comprises a reservoir body comprising plural reservoirs arranged in a plane-like state for storing a drawn fluid and communicating with the nozzles, and an increasing/decreasing device for increasing and decreasing pressure within the reservoirs and the nozzles in a manner that draws or discharges the fluid.

17. An apparatus for an integrated process of magnetic particles according to claim 16, wherein said increasing/decreasing device comprises a sliding body capable of moving vertically to and from the reservoir body, and sliding projections arranged in a plane-like state, projecting downward from the sliding body and capable of sliding through the nozzles in such a manner that the pressure within the reservoirs or nozzles increases or decreases.

18. An apparatus for an integrated process of magnetic particles according to claim 17, wherein said sliding projections are formed to have a two-step structure comprising a larger diameter section capable of sliding through the reservoir, and a smaller diameter section capable of extending along the axes of the larger diameter section and sliding through the nozzle communicating with the reservoir.

19. An apparatus for an integrated process of magnetic particles according to claim 16, wherein said nozzles comprise a tip capable of being mounted to and dismounted from the drawing/discharging device.

20. An apparatus for an integrated process of magnetic particles according to claim 19, comprising a pushing body having pushing pipes inserted from the upper side of the reservoirs into the reservoirs and capable of pushing the nozzles out of the reservoirs, wherein the nozzles are detachably mounted to the reservoirs while being inserted from the lower side of the reservoirs, and the increasing/decreasing device comprises a sliding body having plural sliding projections projecting downward, capable of sliding through the pushing pipes and capable of moving vertically to and from the reservoirs respectively, in a manner that the pressure within the reservoirs or nozzles can be increased or decreased.

21. An apparatus for an integrated process of magnetic particles according to claim 19, wherein said nozzles are detachably mounted to the lower part of the reservoirs and are inserted to a predetermined depth in the reservoirs, sliding projections can slide to a depth of the installation depth of the nozzles in the reservoirs, and a projecting lip part is projected from the outer side of the nozzles exposed under the magnetic force device for mounting and dismounting, and a stroke-down plate provided with plural small hole parts with respective diameters larger than that of the nozzles and smaller than that of the lip parts is mounted between the magnetic force device and the lip parts in a way that the hole parts take insertion of the nozzles and the nozzles can be detached by moving the stroke-down plate down.

22. An apparatus for an integrated process of magnetic particles according to claim 17, wherein an inner wall of the upper part of said reservoir is formed to be cylindrical, and that of the lower part of said reservoir is formed to be funnel-shaped and is connected with said nozzles.

23. An apparatus for an integrated process of magnetic particles according to claim 16, wherein a cleaning liquid can be poured into each reservoir from a passage mounted in the top or side of the reservoir body.

24. An apparatus for an integrated process of magnetic particles according to claim 1, comprising a light measuring device for receiving light from all the vessels or plural liquid containing parts arranged in a plane-like state, simultaneously or all together and measuring the strength of the light or processing it as an image in order to measure a state of light emission.

25. An apparatus for an integrated process of magnetic particles according to claim 24, wherein the light measuring device comprises plural receiving components arranged in a plane-like state, mounted at places corresponding to the liquid containing parts and having the same number as that of the liquid containing part, and shading fences mounted between neighboring receiving components for preventing light entering to other than the corresponding liquid containing part.

26. An apparatus for an integrated process of magnetic particles, comprising:

a drawing/discharging device for drawing and discharging a fluid;

plural nozzles arranged in a plane-like state and passing the fluid there through while drawing and discharging;

a magnetic force device for applying and removing a magnetic field to and from the nozzles respectively in a manner that the neighborhood of each nozzle exterior remains stationary, wherein said magnetic force device comprises an insulating device for preventing heat generated by magnetization or generation of a magnetic field from being transmitted toward the nozzle; and a ventilator for sending air to the magnetic force device or the neighborhood thereof.

27. An apparatus comprising:

a plurality of nozzles for passing fluid; and a magnetic field generator which can generate a magnetic field that is effective within the nozzles, the magnetic field generator comprising a part which has:

a plurality of first openings for receiving the nozzles; and a plurality of second openings which are larger than and are each disposed adjacent to and communicate with a respective one of the first openings, so that the nozzles can each be inserted into and withdrawn from a respective one of the second openings, and can each be moved between one of the first openings and the second opening which communicates therewith.

28. An apparatus according to claim 27, further comprising a fluid flow portion cooperable with the nozzles for effecting fluid flow through the nozzles.

29. An apparatus according to claim 28, wherein each of the nozzles has therethrough a fluid flow opening, and the fluid flow portion has a plurality of movable projections which are each slidable within the fluid flow opening of a respective nozzle.

30. An apparatus according to claim 27, wherein the magnetic field generator has one of a permanent magnet and an electromagnetic, which is coupled to the part of the magnetic field generator.

31. An apparatus according to claim 30, wherein the part of the magnetic field generator has two spaced plates which are each coupled to the one of the permanent magnet and the electromagnetic in a manner so that the plates have opposite magnetic polarities when the magnetic field generator is generating a magnetic field, each of the two plates having the first and second openings extending therethrough.

32. An apparatus according to claim 27, wherein the part of the magnetic field generator member has, adjacent each of the first openings therein, a pair of portions which are spaced, and which have opposite magnetic polarities when the magnetic field generator is generating a magnetic field.

33. An apparatus according to claim 32, wherein the part of the magnetic field generator has two spaced plates which have opposite magnetic polarities when the magnetic field generator is generating a magnetic field, which each have the first and second openings extending therethrough, and which each have a plurality of projections extending toward the other thereof, the portions of each pair being two of the projections that are each provided on a respective plate.

34. An apparatus according to claim 33, wherein the projections on each plate have an end which is spaced from the other plate by a first distance, and wherein the ends of the projections of each pair are spaced from each other by a second distance less than the first distance.

35. An apparatus according to claim 27, wherein the part of the magnetic field generator has a plurality of spaced and approximately parallel column portions, and each column portion has along each side thereof a plurality of spaced protrusions which each project toward one of the protrusions on an adjacent column portion, each of the first openings being a region between ends of a respective pair of the protrusions, each of the second openings being a region between two column portions which is offset from the protrusions on the column portions, and the protrusions of each pair having opposite magnetic polarities when the magnetic field generator is generating a magnetic field.

36. An apparatus according to claim 27, further comprising a vessel having therein a plurality of holes into which the nozzles can be inserted.

37. An apparatus according to claim 36, further comprising a light measuring portion for receiving light from the vessel in order to measure a state of light emission which is a function of substances in the respective holes of the vessel.

* * * * *